US006284910B1

(12) United States Patent
Spielmann et al.

(10) Patent No.: US 6,284,910 B1
(45) Date of Patent: Sep. 4, 2001

(54) FARNESYL PYROPHOSPHATE ANALOGS

(75) Inventors: Hans Peter Spielmann; Douglas A. Andres; Kareem A. H. Chehade, all of Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/461,002

(22) Filed: Dec. 15, 1999

Related U.S. Application Data

(60) Provisional application No. 60/112,208, filed on Dec. 15, 1998.

(51) Int. Cl.[7] .......................................................... C07F 9/08
(52) U.S. Cl. .............................................. 558/152; 560/20
(58) Field of Search ................................ 564/15; 562/20; 558/152

(56) References Cited

U.S. PATENT DOCUMENTS

| 5,212,164 | 5/1993 | Biller et al. | 514/108 |
|---|---|---|---|
| 5,298,655 | 3/1994 | Anthony et al. | 562/598 |
| 5,352,705 | 10/1994 | Deana et al. | 514/630 |
| 5,362,906 | 11/1994 | Anthony et al. | 562/23 |
| 5,504,115 | 4/1996 | Deana et al. | 514/616 |
| 5,631,280 | 5/1997 | Ciccarone et al. | 514/416 |
| 5,631,401 | 5/1997 | Stein et al. | 562/451 |
| 5,691,349 | 11/1997 | Mallion et al. | 514/305 |
| 5,710,171 | 1/1998 | Dinsmore et al. | 514/396 |

FOREIGN PATENT DOCUMENTS

| 534546 | 3/1993 | (EP) | C07F/9/38 |
|---|---|---|---|

OTHER PUBLICATIONS

CA:131:70267 abs of Tennen Yuki Kagobutsu Toronkai Koen Yoshishu 39th pp 481–486 by Maki et al, 1997.*
CA:122:127368 abs of Chem Lett by Maki et al (10) pp 1841–1844, 1994.*
CA:74:84267 abs of J Biol Chem by Troy 246(1) pp 118–133, 1971.*
CA:75:6133 abs of J Amer Chem Soc by Poulter et al 93(7) pp 1783–1785, 1971.*
CA:129:245298 abs of Bioorg Med Chem by Holstein et al 6(6) pp 687–694, 1998.*
CA:125:76276 abs of Mol Pharmacol by Dansei et al 49(6) pp 972–979, 1996.*
T. Baba et al., Photoaffinity Labeling of Undecaprenyl Pyrophosphate Synthetase with a Farnesyl Pyrophosphate Analogue, Journal of Biological Chemistry, 260(19), 10467–73, 1985.
I. Gaon et al., Photoactive Analogs of Farnesyl Pyrophosphate Containing Benzoylbenzoate Esters: Synthesis and Application to Photoaffinity Labeling of Yeast Protein Farnesyltransferase, Journal of Organic Chemistry, 61(22), 7738–45, 1996.
R.L.Edelstein et al., Photoaffinity Labeling of Yeast Farnesyl Protein Transferase and Enzymatic Synthesis of a Ras Protein Incorporating a Photactive Isoprenoid, Biochemical and Biophysical Research Communications, 235(2), 377–382, 1997.
S. Ayral–Kaloustian et al., Annual Reports in Medicinal Chemistry 31, Chapter 18, Ras Farnesyl Transferase Inhibitors, 171–180, 1996.

\* cited by examiner

*Primary Examiner*—Jean F. Vollano
(74) *Attorney, Agent, or Firm*—McDermott, Will & Emery

(57) ABSTRACT

The post-translational addition of a farnesyl moiety to the Ras oncoprotein is essential for its membrane localization and is required for both its biological activity and ability to induce malignant transformation. The present invention describes design and synthesis of a farnesylpyrophosphate (FPP) analog, 8-anilinogeranyl pyrophosphate (AGPP) that is transferred to Ras by farnesyltransferase (FTase), in which the ω-terminal isoprene unit of the farnesyl group has been replaced with an aniline functionality. AGPP potently inhibited FTase activity in vitro ($IC_{50}=0.6$ μM) and is highly selective showing little inhibitory activity against either geranylgeranyl-protein transferase type I (GGTase I) ($IC_{50}=31$ μM) or the utilization of FPP by the enzyme squalene synthase ($IC_{50}=1000$ μM). Kinetic analyses suggest that AGPP acts as a competitive inhibitor of FTase with respect to FPP. In vitro studies using [$^3$H]AGPP show that the analog was appropriately transferred by FTase to Ras. Derivitization of AGPP with a bulky iodo group on the aniline ring does not significantly alter its biochemical properties. These data indicate that the modified molecules are the first truly transferable analogs of FPP and open the door to additional analogs to probe the biological function of protein farnesylation.

17 Claims, 10 Drawing Sheets

FARNESYL PYROPHOSPHATE ANALOGS

This application claims priority from provisional application 60/112,208, filed on Dec. 15, 1998.

FIELD OF THE INVENTION

The present invention relates to farnesyl pyrophosphate analogs and their use in modulating cellular chemistry. More specifically, the invention relates to unsubstituted and substituted anilinogeranyl pyrophosphates (AGPP), unsubstituted and substituted benzyloxyalkylisoprenyl pyrophosphates, the processes of making the same, intermediates for use in the process of making the same, and the methods of using the FPP analogs in substitution for farnesyl pyrophosphate (FPP) or as farnesyl transferase inhibitors (FTIs).

BACKGROUND OF THE INVENTION

Farnesyl pyrophosphate 1 (FPP) and its $C_{20}$ homolog, geranylgeranyl pyrophosphate (GGPP) are isoprenoids that are involved in a number of cellular processes including cholesterol biosynthesis, glycoprotein biosynthesis, vitamin and cofactor synthesis and protein prenylation. Recently, the enzyme farnesyltransferase (FTase) which can utilize FPP or GGPP as a substrate depending on the nature of the β subunit, has attracted considerable interest as a possible target for the design of chemotherapeutic agents.

An area of interest is the continued search for proteins that are post-translationally modified in cells as part of normal metabolism. Farnesylation has been shown to be required for the normal function of various proteins including Ras.

Mutated forms of the cellular Ras genes are among the most common genetic abnormalities in human cancer, occurring in 30% of all neoplasms. This frequency indicates an important role for aberrant Ras function in carcinogenesis (1). Ras proteins are synthesized as cytosolic precursors which localize to the inner leaflet of the plasma membrane only after undergoing a series of well defined posttranslational modifications (2). The first and obligatory step in this processing is the transfer by protein farnesyltransferase (FTase) of the 15-carbon isoprene farnesyl from farnesylpyrophosphate (FPP) to a cysteine residue located at the Ras C-terminus via a thioether linkage (2,3). This Cys residue forms part of the prenylation recognition sequence, CAAX (where A is an aliphatic residue and X is most often Met, Ser, or Gln), present in all Ras proteins (4). Prenylation is followed by proteolytic removal of the COOH-terminal tripeptide and carboxymethylation of the now terminal, prenylated cysteine (2). These modifications render the C-terminus hydrophobic, which is thought to promote the association of these proteins with the plasma membrane. Studies employing site-directed mutants within the Ras CAAX motif (5,6) or inhibitors of 3-hydroxyl-3-methylglutaryl CoA reductase (7), the rate limiting enzyme in isoprenoid biosynthesis, have demonstrated that isoprenylation is required for Ras proteins to become membrane associated and to induce cellular transformation.

Three distinct enzymes responsible for protein isoprenylation have been isolated and biochemically characterized (2). In addition to FTase, two geranylgeranyl-transferases (GGTases) have been isolated and have been shown to modify specific protein substrates. While the CAAX GGTase (also known as GGTase-1) geranylgeranylates proteins which end in a CAAL sequence, where C is cysteine, A is usually an aliphatic amino acid, and L is leucine (8,9), the Rab GGTase (also known as GGTase-2) catalyzes the attachment of two geranylgeranyl groups to paired carboxyl-terminal cysteines in members of the Rab family of GTP-binding proteins (10). These proteins terminate in a CC or CXC motif.

A number of basic issues pertaining to the biological function of protein isoprenylation, and the contribution of lipid modification in general, remain to be answered. While farnesylation of Ras is absolutely required for its biological effects and membrane localization, it is unknown whether the prenyl group functions as a hydrophobic membrane association signal (11–16) or by targeted protein-protein recognition (17,18). The functional significance of protein farnesylation versus geranylgeranylation to the biological activity of prenylated proteins is also unknown. Studies employing inhibitors of FTase have highlighted the importance of isoprenylation to the membrane association and activity of the Ras family of signal transduction proteins. However, inhibition of protein prenylation precludes relating the effects of many of the downstream events such as further modification of the target protein by palmitoylation, proteolysis and carboxymethylation to the biological function of Ras.

Extensive research studies have established an important contribution of aberrant Ras function to human carcinogenesis (88, 89) Consequently, there is considerable interest in the development of inhibitors of Ras function for use in cancer treatment. Since Ras function is absolutely dependent on lipid modification and tight association with the plasma membrane, the development of drugs that block Ras membrane association has attracted the greatest interest (89–91). FTase has proven to be a biochemical target for the development of inhibitors of post-translational processing of Ras that act as potent anti-Ras drugs.

Several general approaches have been employed in the identification and development of specific FTase inhibitors (reviewed in 88). First, high throughput random screens have been used to identify natural or library compounds that inhibit the ability of FTase to catalyze the addition of farnesyl to recombinant Ras in vitro. Second, Ras CaaX tetrapeptide sequences alone are sufficient to signal modification by farnesylation and can serve as potent inhibitors of FTase activity in vitro. Therefore, a variety of CaaX-based peptidomimetic compounds have been synthesized. Consequently, the potent and selective FTIs identified to date include a diverse collection of structurally unrelated compounds. However, the structural requirements of the prenyl group have not been uncovered.

The initial characterization of FTIs was done in fibroblast model systems transformed by oncogenic H-Ras (92, 93). These studies clearly showed that FTIs can potently and specifically inhibit H-Ras farnesylation, without affecting the modification of geranylgeranylated proteins. FTI inhibition of H-Ras processing correlated directly with inhibition of H-Ras-induced signaling, morphologic and growth transformation (94). Similar dramatic results were seen in in vivo tumor models using Ras-transformed rodent cells grown as xenografted tumors in nude mice (95), and in viral H-Ras transgenic mice in which salivary and mammary tumors occur stochastically in a high percentage of mice carrying the transgene (96, 97). An unexpected, but desired, aspect of these studies is the apparent lack of normal cell toxicity. This was unexpected because farnesylation is required for normal Ras function, which is critical for normal cell viability (97). The reason(s) for the relative resistance of normal cells to FTIs is presently not known.

Because of previous finding that FTIs were capable of inhibiting Ras transformation in animal model systems, and because of the widespread tendency to view FTIs as Ras inhibitors rather than FTase inhibitors, many investigators assumed that human tumors cells that contained mutated Ras proteins would be more sensitive to FTI action than those that did not. However, studies have shown that ras mutation status is not predictive of FTI sensitivity (98). Indeed, it is clear that these drugs interfere with the processing of other farnesylated proteins in addition to Ras. There is now evidence that FTIs may block Ras transformation, in part, by inhibiting the function of other farnesylated proteins, one or more of which may represent the critical target for FTI action (87, 99, 100).

It is clear that the cellular mechanism by which FTIs exert their biological activity is incompletely understood (88). Two central issues appear that must be addressed before the biochemical mechanism by which FTIs function can be understood. First, it is necessary to understand the biological significance of the isoprenoid lipid in the context of the function of a fully processed prenyl protein. For FTIs, the natural targets for this analysis are the Ras oncoproteins. Second, as outlined above, it is likely that FTIs inhibit the farnesylation of additional cellular proteins, many of which remain to be identified, and are likely to depend upon prenylation for some aspect of their function. Therefore, the key to applying FTase-based pharmacological intervention is a thorough understanding of the in vivo farnesylation pathways. Knowledge of the complete array of cellular protein substrates and substrate specificities for FTase and the cellular role of the isoprenoid moiety will be critical in improving the design and action of effective FTIs.

Prenyl analogs and FTIs have contributed to the understanding of prenylation and such information is useful in the design and evaluation of therapeutics. The mechanism underlying FTI action is of interest for several reasons. The action of the drug is likely to be secondary to the specific inhibition of Ras farnesylation, suggesting that additional farnesylated proteins yet to be identified or assigned a cellular function play a critical role in the biology of transformation (90). Second, several FTIs are currently entering phase I trials as anticancer drugs in humans and rational clinical development will depend on understanding the biochemical basis for their inhibition of cell growth.

SUMMARY OF THE INVENTION

The present invention provides for the preparation and functional characterization of unsubstituted anilinogeranyl pyrophosphate (AGPP), substituted anilinogeranyl pyrophosphate, unsubstituted and substituted benzyloxy-alkylisoprenyl pyrophosphate, and pharmaceutically acceptable salts thereof, which meet the criteria set forth for FPP analogs (i.e. FTase substrates and inhibitors) in the Background of the Invention. AGPP and other FPP analogs of the invention are recognized and transferred to Ras by FTase with in vitro kinetic properties that are indistinguishable from those of FPP. AGPP can be modified by iodination without significantly altering these properties, allowing synthesis of additional analogs. Other analogs of FPP wherein the ω-isoprenyl moiety is replaced by either a functionalized aniline or a functionalized benzyloxy group may be synthesized by alternate routes. Finally, the present invention reveals that AGPP and other FPP analogs of the invention are poorly recognized by, and transferred to, substrate by GGTase I and are neither substrates for, nor inhibitors of, squalene synthase, suggesting a high degree of selectivity toward FTase in vivo. Thus, the present invention provides for a method of using AGPP as a substrate for FTase in the prenylation of Ras.

It is accordingly an aspect of the invention to provide a FPP analogs which would be efficiently utilized by FTase, allow for further derivatization for high specific activity labeling or cross linkers to be designed, and that would be recognized and transferred to FTase substrate proteins with an activity approaching that of FPP. Such FPP mimetic molecules can interfere with other cellular events, while acting as non FTI anti-Ras molecules.

FPP analogs of the invention also inhibit the function of FTase.

It is accordingly another aspect of the invention to provide FPP analogs that are inhibitors of farnesyl transferase and therefore affect intracellular processes involving the transfer of farnesyl to intracellular proteins essential to the functioning of those intracellular proteins.

Conceptually, FPP can be viewed as a four-section molecule. The α-isoprene and the pyrophosphate moiety remain invariant in all of the FPP analogs of the present invention because an allylic pyrophosphate is essential for FTase catalyzed transfer to protein substrate (117).

The structure of FPP:

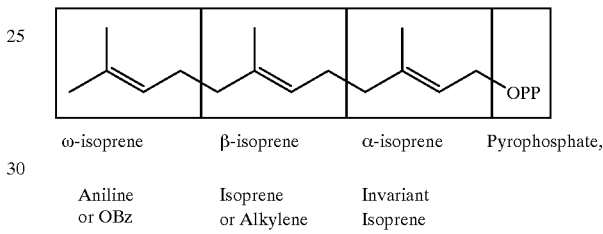

| ω-isoprene | β-isoprene | α-isoprene | Pyrophosphate, |
|---|---|---|---|
| Aniline or OBz | Isoprene or Alkylene | Invariant Isoprene | |

The captions below the α-, β-, and ω-isoprene units of FPP above represent the general substitutions made for the isoprene unit in compounds according to the invention, wherein aniline may be unsubstituted or substituted, OBz is a benzyloxy group, which is unsubstituted or substituted as indicated in Formulae I-II below, and alkylene is an alkylene linking group having 1 to 10 carbon atoms.

DETAILED DESCRIPTION OF THE INVENTION

Figure 1:
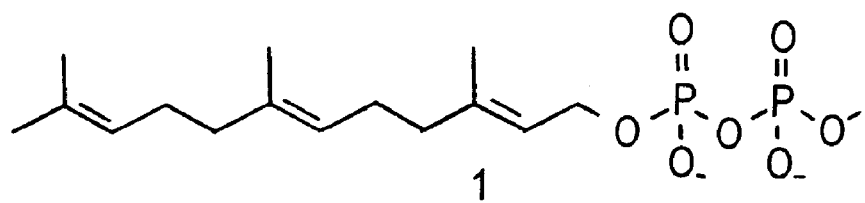
FIG. 1. Structure of farnesylpyrophosphate 1, geranylgeranylpyrophosphate 2, 8-anilinogeranyl pyrophosphate (AGPP) 3a, p-iodo-8-anilinogeranyl pyrophosphate (AGPP) 3b.
Figure 1:
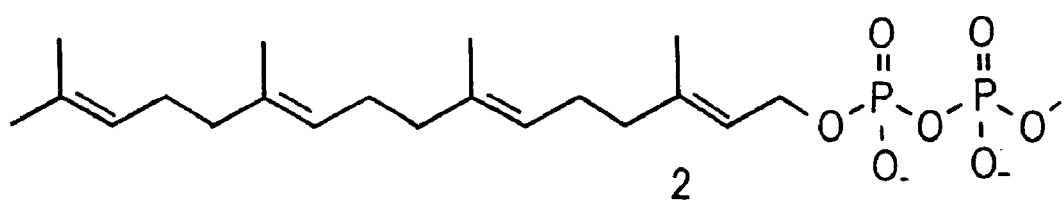
Figure 1:
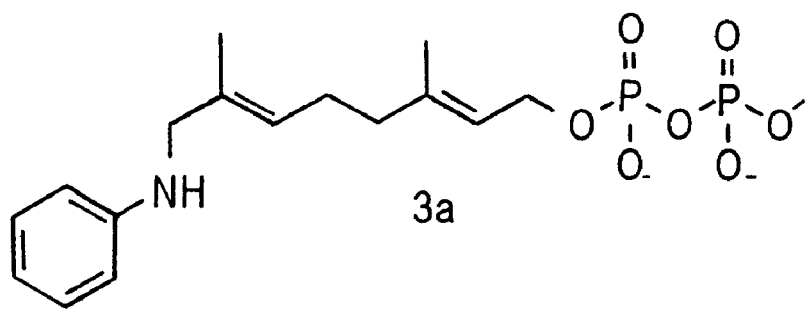
Figure 1:
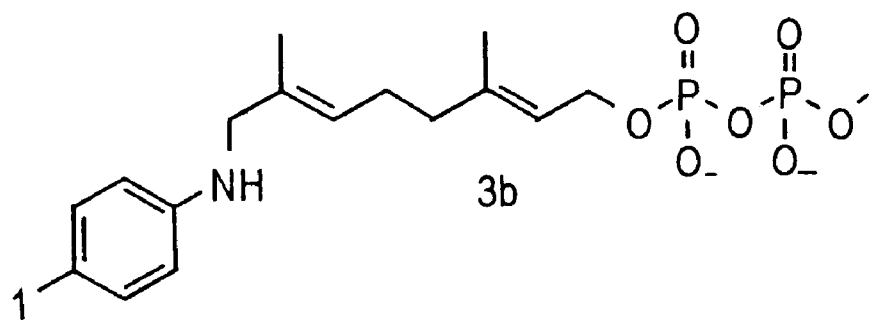

The farnesyl pyrophosphate analogs of this invention are useful as substrates for FTase, and in particular for FTase mediated isoprenylation of proteins such as the Ras protein.

The farnesyl pyrophosphate analogs of the invention are also useful as farnesyl transferase inhibitors (FTIs).

The farnesyl pyrophosphate analogs of this invention may be prepared in free base form, or they may be prepared in the form of pharmaceutically acceptable salts according to the conventional practice in the pharmaceutical arts. Likewise, they can be prepared in pharmaceutically acceptable form in combination with carriers, adjuvants, excipients and the like. The dosages of the compounds, their pharmaceutically acceptable salts and compositions containing them may be determined by conventional clinical methods in the art.

The farnesyl pyrophosphate analogs according to this invention may be employed for the treatment of human and non-human patients in which modulation of farnesyl pyrophosphate or FTase inhibition is desired. As farnesyl pyrophosphate is involved in a number of cellular processes including cholesterol biosynthesis, glycoprotein biosynthesis, vitamin and cofactor synthesis and protein prenylation, the compounds of the present invention are useful for affecting such cellular processes and disease states caused thereby. Also, as FTase is involved in farnesylation of important intracellular proteins such as Ras, the compounds of the present invention are useful for treating disease states in which farnesylation of important intracellular proteins such as Ras is implicated, such as cancer.

Recently, the enzyme farnesyltransferase (FTase) which can utilize FPP or GGPP as a substrate, depending on the nature of the β subunit, has attracted considerable interest as a possible target for the design of chemotherapeutic agents. The present invention thus contemplates a method of treating conditions that are affected by FPP and its analogs.

The compounds of this invention are illustrated by general formula I:

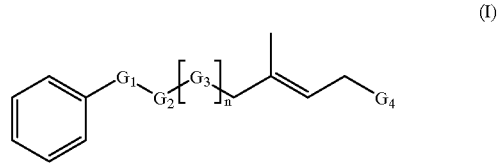

(I)

Wherein the phenyl ring is unsubstituted or substituted. Suitable substituents for the phenyl ring are, for example, H, halo, $NO_2$, $NH_2$, $NHR_7$, $N(R_7)_2$, $N(R_7)_3^+$, $N_3$, OH, $OR_7$ and optionally substituted $C_1$ to $C_8$ alkyl. $R_7$ is $C_{11}$–$C_8$ alkyl (e.g. methyl, ethyl, i-propyl, n-propyl, n-butyl, i-butyl, s-butyl, t-butyl, n-pentyl, etc.) or $C_1$–$C_8$ alkanoyl (e.g. formyl, acetyl, propanoyl, etc.). $G_4$ is OPP, $OR_8$, or S-linked cysteine (which may be in the R, S or racemic configuration). And $R_8$ is a suitable hydroxy protecting group.

$G_1$ is $NR^6$ or —$CH_2$—O—;

$G_2$ is: —$CH_2$—, —$CH_2CH_2$— or

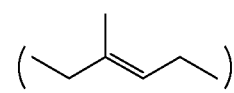

$G_3$ is: —O—$CH_2$—$CH_2$— or —$CH_2$—;

n is an integer of 0 to 14, inclusive;

$R_6$ is H or alkyl.

Throughout this description, OPP is the pyrophosphate group:

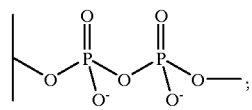

In general, according to the present invention, alkyl is a $C_1$ to $C_8$ alkyl substituent group. Examples of alkyl are methyl, ethyl, i-propyl, n-propyl, n-butyl, t-butyl, s-butyl, i-butyl, pentyl, etc. Suitable optional substitutents for such alkyl groups may be one or more substituents such as amine, alkyl amine, dialkylamine, nitrile, and hydroxy. Preferred substituted alkyl groups are hydroxymethyl, hydroxyethyl, aminomethyl, aminoethyl, $(NC)CH_2-$, and $(NC)CH_2CH_2-$.

A preferred embodiment of the above compounds of formula I is illustrated by formula II:

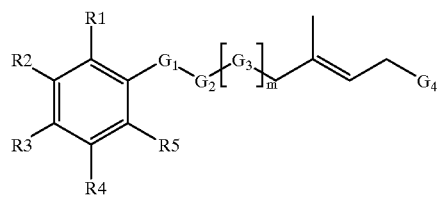

(II)

wherein $R_1$, $R_2$, $R_3$, $R_4$, and $R_5$ are, for example, H, halo, $NO_2$, $NH_2$, $NHR_7$, $N(R_7)_2$, $N(R_7)_3^+$, $N_3$, OH, $OR_7$, $C_1$ to $C_8$ alkyl, amino $C_1$-$C_8$ alkyl, hydroxy $C_1$-$C_8$ alkyl, nitrile $C_1$-$C_8$ alkyl, etc. $G_1$, $G_2$, $G_3$, and $G_4$ are defined in formula I. The variable m is an integer of 0 to 5. $R_7$ is $C_1$-$C_8$ alkyl (e.g. methyl, ethyl, i-propyl, n-propyl, n-butyl, i-butyl, s-butyl, t-butyl, n-pentyl, etc.) or $C_1$-$C_8$ alkanoyl (e.g. formyl, acetyl, propanoyl, etc.) etc.

Another preferred embodiment of compounds of formula I is illustrated by formula III:

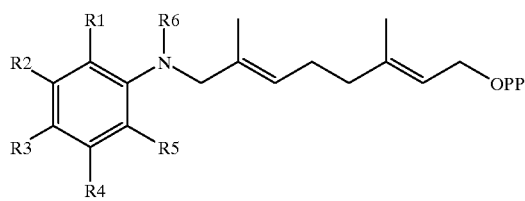

(III)

wherein $R_1$, $R_2$, $R_3$, $R_4$, and $R_5$ are, for example, H, halo, $NO_2$, $NH_2$, $NHR_7$, $N(R_7)_2$, $N(R_7)_3^+$, $N_3$, OH, $OR_7$, $C_1$-$C_8$ alkyl, amino $C_1$-$C_8$ alkyl, hydroxy $C_1$-$C_8$ alkyl, nitrile $C_1$-$C_8$ alkyl, etc. $R_7$ is $C_1$-$C_8$ alkyl (e.g. methyl, ethyl, i-propyl, n-propyl, n-butyl, i-butyl, s-butyl, t-butyl, n-pentyl, etc.) or $C_1$-$C_8$ alkanyl (e.g. formyl, acetyl, propanoyl, etc.) etc., and alkyl is $C_1$ to $C_8$ alkyl, for example methyl, ethyl, n-propyl, i-propyl, n-butyl, i-butyl, s-butyl, t-butyl, n-pentyl, etc.

An even more preferred embodiment of compounds of formula III is represented by formula IV:

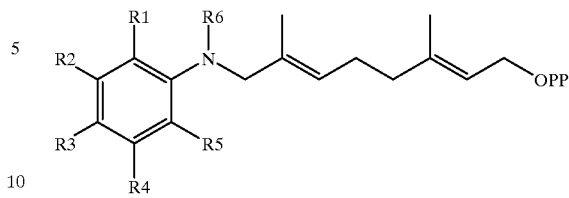

(IV)

wherein $R_1$, $R_2$, $R_4$, and $R_5$ are H or F;

$R_3$ is H, $NO_2$, I, F or $N_3$; and $R_6$ is H, methyl or ethyl.

Another preferred compound of formula I is represented by formula 11:

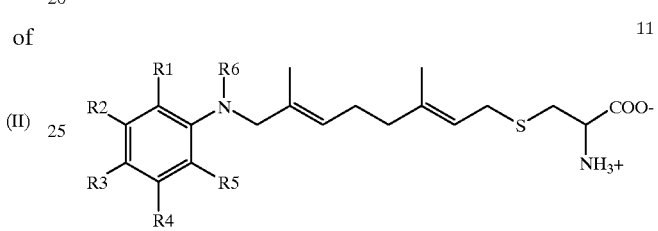

11 wherein $R_1$–$R_6$ are defined above in formula I and the moiety:

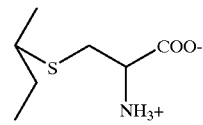

is the aforementioned S-linked cysteine, which may be in the R, S or racemic configuration, more preferably in the S-configuration (i.e. derived from the naturally occurring cysteine).

Preferred compounds of formula 11 are those in which, $R_1$–$R_6$ are H and the S-linked cysteine is in the S-configuration (compound 11a).

Even more particularly preferred compounds of formula IV include:

(1) 8-aniline-3,7-dimethyl-2,6-octadiene pyrophosphate (AGPP);

(2) 8-(4-nitroaniline)-3,7-dimethyl-2,6-octadiene pyrophosphate;

(3) 8-(4-iodoaniline)-3,7-dimethyl-2,6-octadiene pyrophosphate;

(4) 8-pentafluoroaniline-3,7-dimethyl-2,6-octadiene pyrophosphate;

(5) 8-(4-azido-2,3,5,6-tetrafluoroaniline)-3,7-dimethyl-2,6-octadiene pyrophosphate; and (6) 8-(N-ethyl-4-azido-2,3,5,6-tetrafluoroaniline)-3,7-dimethyl-2,6-octadiene pyrophosphate.

Another preferred embodiment of the compounds of formula I is exemplified by the compounds of formula V:

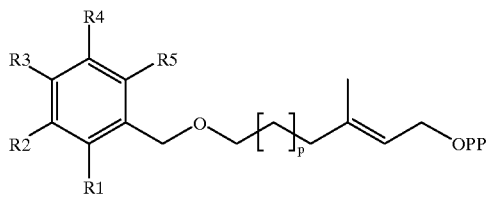

(V)

wherein $R_1-R_5$ are as defined in formula I, p is an integer from 1 to 10 and OPP stands for the pyrophosphate group.

Particularly preferred compounds of formula V are exemplified by formula VI: wherein $R_1-R_5$ are as in formula V, above; q is an integer of 1 to 5, inclusive; and OPP is the

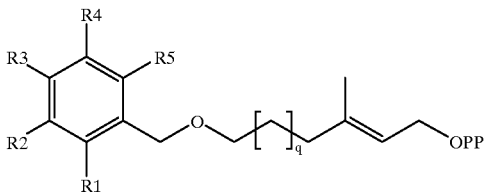

(VI)

pyrophosphate group.

Particularly preferred compounds of formula VI include compounds exemplified by formula VII:

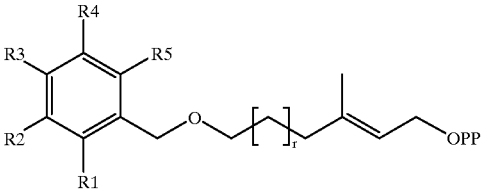

(VII)

wherein $R^3$ is as defined in formula VI other than H; and $R^1$, $R^2$, $R^4$, and $R^5$ are as defined in formula VI; r is an integer of 1 to 5, inclusive; and OPP is the pyrophosphate group.

Particularly preferred compounds of formula V have been synthesized, including:

6-benzyloxy-3-methyl-2-hexene pyrophosphate (12);
7-benzyloxy-3-methyl-2-heptene pyrophosphate (13);
8-benzyloxy-3-methyl-2-octene pyrophosphate (14);
9-benzyloxy-3-methyl-2-nonene pyrophosphate; and
10-benzyloxy-3-methyl-2-decene pyrophosphate.

Another preferred embodiment of compounds of formula I is exemplified by the compounds of formula VIII:

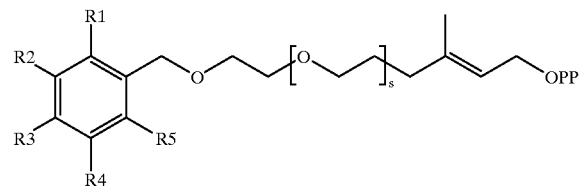

(VIII)

wherein $R_1-R_5$ are as defined in formula I, preferably $NO_2$, $N_3$, $NH_3$, halo, such as F, Cl, Br and I, 1–8 carbon alkyl such as methyl, ethyl, i-propyl, n-propyl, i-butyl, n-butyl, s-butyl, t-butyl, etc. The variable s is an integer from 1 to 5.

Another preferred embodiment of compounds of formula II includes the compounds of formula IX:

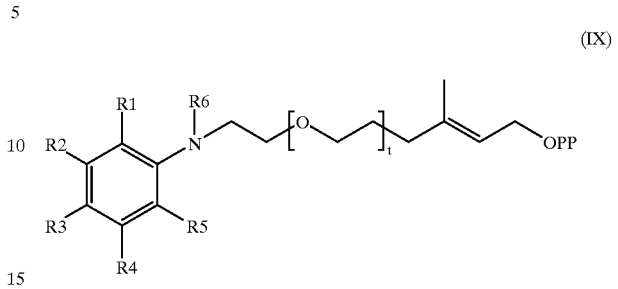

(IX)

wherein $R_1-R_5$ are is as defined in formula I, t is an integer from 1 to 5 and $R^6$ is hydrogen or $C_1-C_8$ alkyl.

Another preferred embodiment of compounds of formula I includes compounds of formula X:

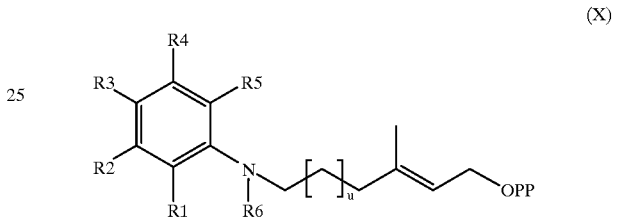

(X)

wherein $R_1-R_6$ are as defined in formula I, above and u is an integer number 1 to 10.

Another aspect of the invention relates to a novel oligo-ether of formula XI:

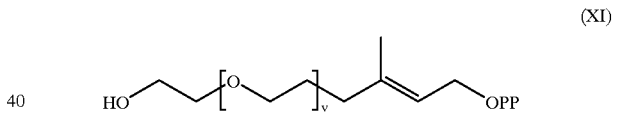

(XI)

wherein v is an integer from 1 to 10, inclusive; and OPP is the pyrophosphate group.

Another aspect of the invention relates to compounds of the formula XII:

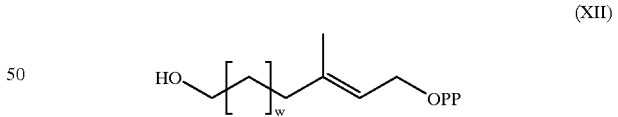

(XII)

wherein w is an integer of 1 to 10, inclusive and OPP is the pyrophosphate group.

Another aspect of the claimed invention relates to allylic diols of formula XIII:

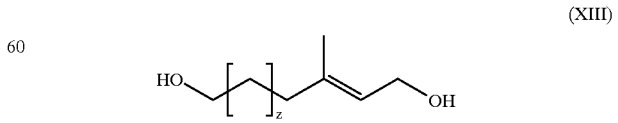

(XIII)

wherein z is an integer of 1 to 14.

Compounds of formula I possess a pyrophosphate group which is acidic under physiologic conditions. The compounds of the invention may therefore be formulated in the form of free acid. They may also be formulated as pharmaceutically acceptable salts by conventional methods well known in the art, such as by combining an acidic compound of the present invention with a physiologically tolerated base. Such bases include alkali or alkaline earth metal hydroxides such as NaOH, KOH, LiOH, etc. Such bases also included organic amines such as dibenzylethylenediamine, trimethylamine, piperidine, pyrrolidine, benzylamine and the like, or a quaternary ammonium hydroxide such as tetramethylammonium hydroxide, and the like.

The compounds and pharmaceutically acceptable salts of the invention may be combined with pharmaceutically acceptable carriers, excipients, adjuvants, and the like, to form pharmaceutical compositions. The pharmaceutical compositions may comprise other physiologically tolerated and/or beneficial compounds. Suitable carriers may be solid, such as binders and cutting agents conventional in the pill, tablet and capsule forming arts, or liquid, such as solvents, diluents and emulsifiers conventional in the parenteral and oral elixir compounding arts.

Pharmaceutical compositions comprising compounds of the invention or pharmaceutically acceptable salts thereof advantageously contain 0.01% to 100% by weight of the compound or a pharmaceutically acceptable salt of the invention, preferably 0.1% to 50%, and even more preferably 1 to 25%.

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaccutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

Compounds of the invention may be synthesized by methods set forth below.

In particular, compounds of formula I may be synthesized by Scheme 1 or Scheme 2, as appropriate.

The compounds of formulae III and 11 can be obtained via Scheme 1.

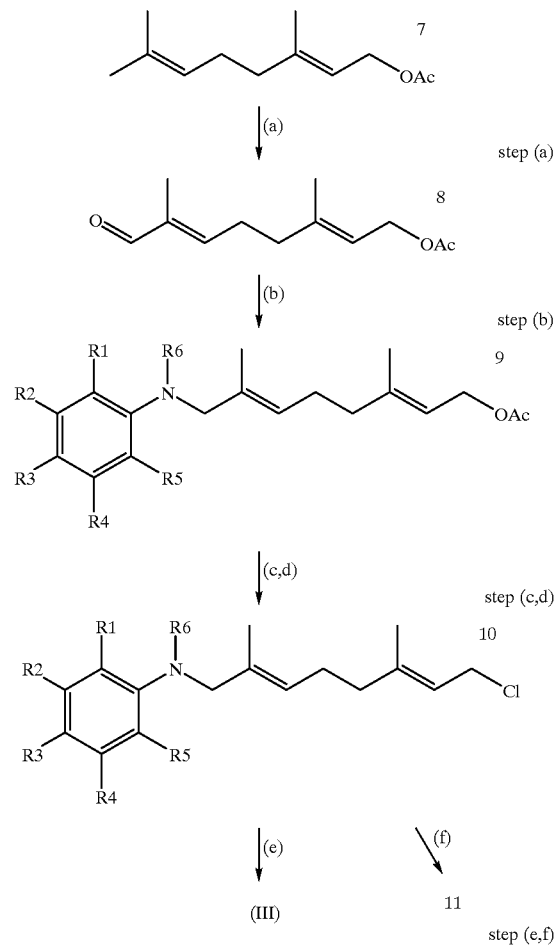

wherein formula $R_1$–$R_6$, III and 11 are as defined above.

Additionally, the compound of formula III may be reacted with iodobeads to form the para-iodoaniline compound (reaction step (g), not depicted above). When a compound of formula III, wherein $R_1$, $R_2$, $R_3$, $R_4$, $R_5$, and $R_6$ are H, the product of such reaction step (g) is the compound 3 (8-(4-iodoaniline)-3,7-dimethyl-2,6-octadiene pyrophosphate).

Reaction Conditions for Scheme 1

(a) tert-butylhydroperoxide, $SeO_2$, salicylic acid, $CH_2Cl_2$;
(b) the unsubstituted or substituted aniline:

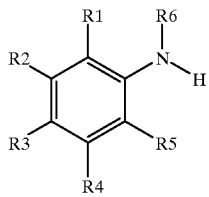

wherein $R_1$–$R_6$ are as indicated in formula III, above, $NaBH(OAc)_3$, HOAc, 1,2-dichloroethane;

(c) $K_2CO_3$, MeOH, $H_2O$;
(d) $(Ph)_3PCl_3$, Hunig's base, $CH_3CN$;
(e) $[(n\text{-butyl})_2N]_3$, $HP_2O_7$, $CH_3CN$;
(f) N-(tert-butoxy carbonyl) cysteine methyl ether;
(g) iodobeads.

Compounds of formula III are based on a geranyl skeleton where the terminal isoprene unit of the farnesyl moiety has been replaced by an anilino functional group. Species 1 through 6 above are six examples of molecules that have been synthesized by the process of Scheme 1. Such compounds possess widely varied functionality, including para-iodoanilino, para-nitroanilino, para-azidoanilino, pentafluoroanilino, and para-azidotetrafluoroanilino groups. The methodology for synthesizing substituted anilino analogs of FPP is robust and versatile. The aniline ring system in these analogs provides a platform for the introduction of a wide variety of functional groups and provides a heteroatom linkage connecting the geranyl pyrophosphate moiety to the phenyl group which replaces the terminal isoprene unit.

The amino linkage is formed by reductive amination of the aniline by the geranyl α-β unsaturated aldehyde (8) with $NaBH(OAc)_3$ to form the lipid portion of the analog 9.

Reductive amination of α-β unsaturated aldehydes to form anilines has not been previously described in the literature. The invention provides for incorporation of anilines with very sensitive functional groups such as aryl azides into the analogs. Previously reported methods to form this linkage either do not work or destroy sensitive functional groups. The presence of the amine precluded the implementation of standard methods (72–74) to convert the lipid allylic alcohol to the desired pyrophosphate via an activated chloride intermediate. The present invention utilizes modified published procedures (75) to convert the allylic alcohol to the corresponding allylic chloride using dichlorotriphenylphosphorane (9→10). The resulting allylic chloride was then converted to the desired pyrophosphate analog 1 and the prenyl-analog-cysteine (AG-cys) 11.

Compounds of formula V, VII and VII may be synthesized by following Scheme 2.

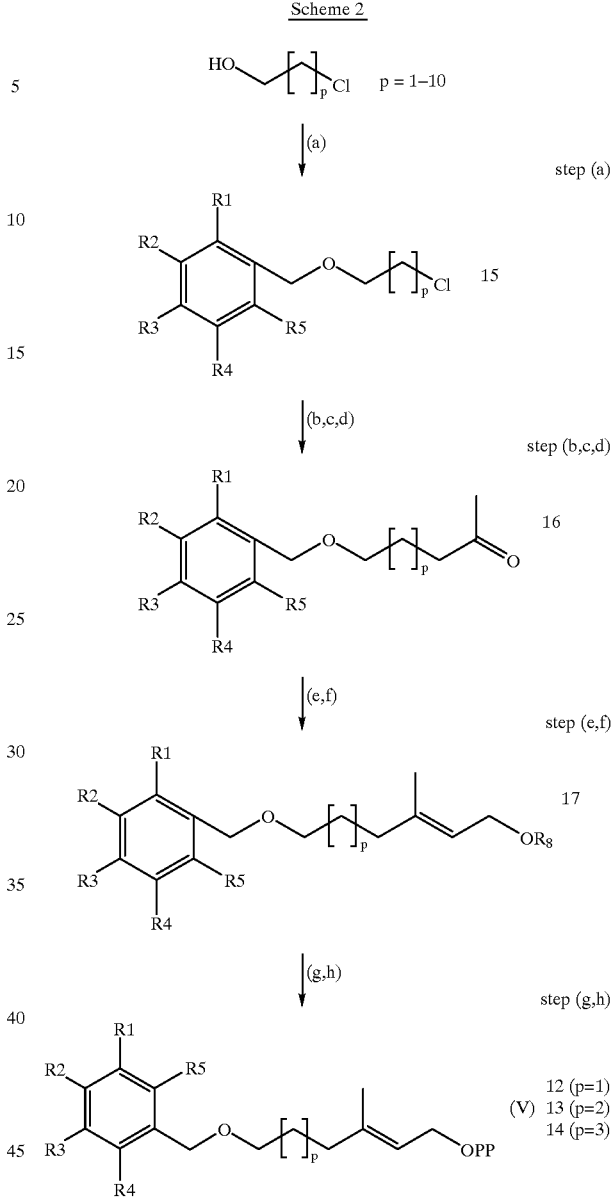

wherein $R_1$–$R_5$ are as defined above for formula V; and suitable choice of p will yield a compound of formula V, VI or VII.

In formula 17, $R_8$ is an hydroxy protecting group.

Scheme 2 Reaction Conditions
(a) benzyl chloride;
(b) NaOH, ethyl acetoacetate;
(c) NaOH;
(d) $H_2SO_4$;
(e) ethyl diisopropylphosphonoacetate, NaH;
(f) LAH;
(g) $(Ph)_3PCl_2$, Hunig's base, $CH_3CN$;
(h) $[(n\text{-Bu})_4N]_3HP_2O_7$, $CH_3CN$.

Compounds of formula V are based on an alkyl allylic pyrophosphate skeleton where the middle isoprene unit of farnesyl moiety is replaced by a variable length aliphatic hydrocarbon chain and the terminal isoprene unit is replaced by either an anilino or a benzyl ether function. These molecules can adopt a greater range of conformations relative to the geranyl type analogs because there are fewer unsaturated bonds in the molecules. In addition, the overall length of the molecule can be adjusted in single methylene increments by changing the length of the hydrocarbon linker. Three examples of these molecules with different lengths of hydrocarbon linker have been synthesized per Scheme 2, taking advantage of all the synthetic lessons learned in the creation of the first class of analogs. The length of the hydrocarbon linker chain is set by the choice of benzyl protected ω-chloro-alkanols 15 used to synthesize the key intermediate ketone 16. This ketone is elaborated to the trans-isoprenoid like allylic alcohol 17 by a Horner-Emmons reaction, followed by reduction of the resulting ester with lithium aluminum hydride (LAH). A wide variety of benzyl protecting groups (benzyl, p-bromobenzyl, p-methoxybenzyl, etc.) are stable to this series of reactions and these alcohols can be converted to the corresponding pyrophosphates via the chloride. The first example 12 is transferred to dansyl peptide by FTase with slow kinetics, showing that this class of analogs represents viable structures for exploring the role of prenyl groups in biological systems.

Compounds of formula VIII can be made by modifying the process of Scheme 2 by substituting compounds of the general formula HO—CH$_2$—(OCH$_2$CH$_2$)$_p$Cl for HOCH$_2$(CH$_2$)$_p$Cl in the first step of scheme 2.

Compounds of formula X may be prepared as depicted in Scheme 3A.

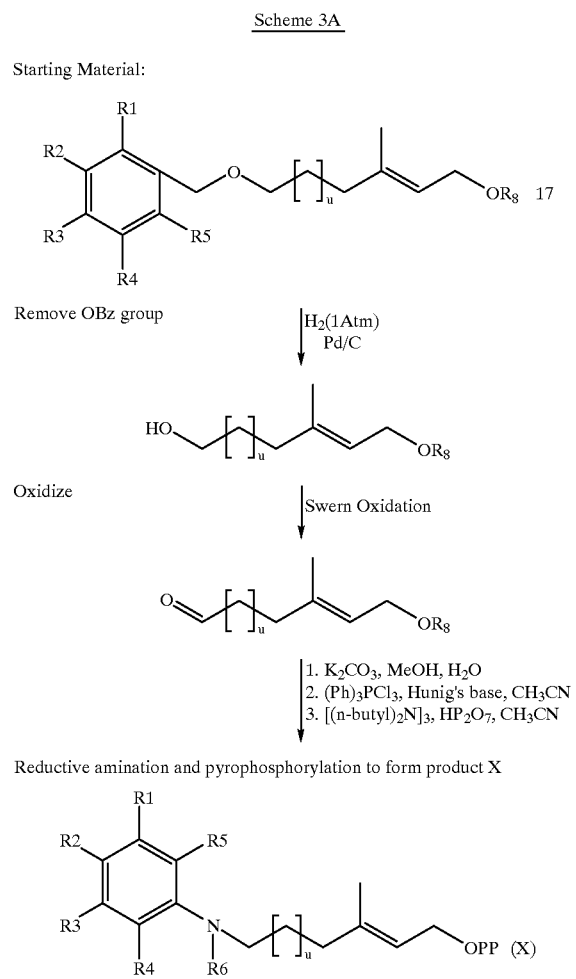

wherein R$_1$–R$_6$, u, and OPP are as defined above in formula X and R$_8$ is an hydroxy protecting group.

This pathway is especially advantageous when the groups R$_1$–R$_5$ on the benzyl group are not stable to the LAH reduction to produce the alcohol.

This pathway may also be used to produce compounds of the formula IX by modifying reaction Scheme 3A. The suitable starting materials, which are modified forms of 17 above, may be produced by the method of Scheme 2, wherein compounds of formula: HOCH$_2$CH$_2$(OCH$_2$CH$_2$)$_t$Cl (t is 1–5) are substituted for the compound of formula HOCH$_2$(CH$_2$)$_p$Cl in Scheme 2. The resulting modified analog of 17 is then subjected to the steps outlined in Scheme 3A to produced IX.

Compounds of formula VI and VII may be produced by the alternate pathway described in Scheme 3B.

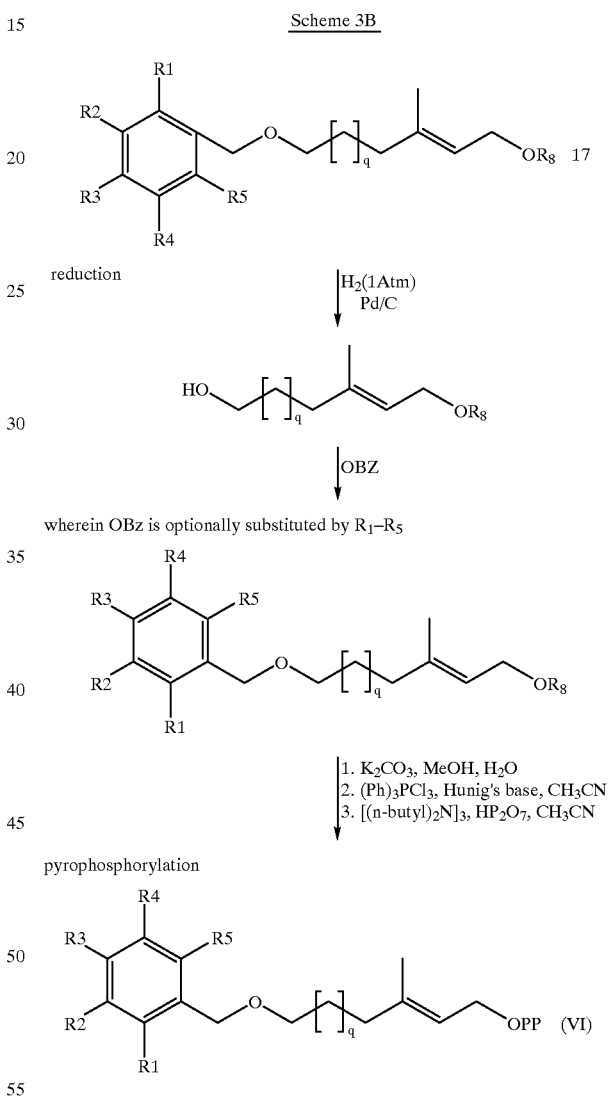

This pathway is especially advantageous when the groups R$_1$–R$_5$ on the benzyl group are not stable to the LAH reduction to produce the alcohol.

This pathway may also be used to produce compounds of the formula VIII by modifying reaction Scheme 3B. The suitable starting materials, which are modified forms of 17 above, may be produced by the method of Scheme 2, wherein compounds of formula: HOCH$_2$CH$_2$(OCH$_2$CH$_2$)$_t$Cl (t is 1–5) are substituted for the compound of formula HOCH$_2$(CH$_2$)$_p$Cl in Scheme 2. The resulting modified analog of 17 is then subjected to the steps outlined in Scheme 3B to produce VIII.

The compounds of formula XIII can be obtained from a compound of formula VI via the pathway of Scheme 4.

Scheme 4

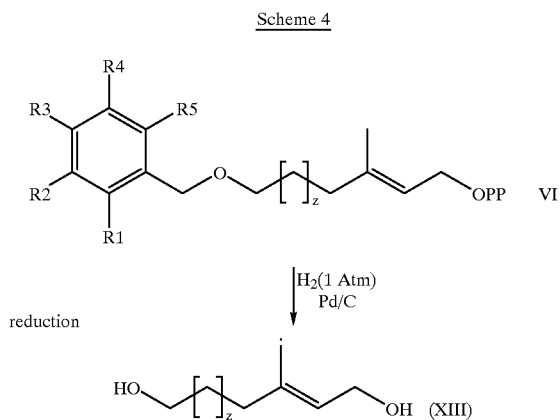

Wherein $R_1$–$R_5$ are as defined in formula VI above; z is 1 to 10 and OPP is the pyrophosphate group.

The corresponding compounds of formula XII may be obtained from the compounds of formula VI by removing the benzyloxy group via mild hydrogenolysis.

The compounds of formula XI can be obtained by blocking the terminal OH group, converting the 1-hydroxy group to the chloride, subjecting the same to pyrophosphorylation and finally removing the terminal OH group.

DETAILED DESCRIPTION OF THE PREFERRED EMBODIMENTS

General Methods—[1-$^3$H]farnesyl pyrophosphate ([$^3$H] FPP, 15 Ci/mmol) and [1-$^3$H]geranylgeranyl pyrophosphate ([$^3$H]GGPP, 15 Ci/mmol) were obtained from American Radiochemical Co. Recombinant wild-type p21$^{Ha-ras}$ protein (p21$^{H-ras}$ CVLS) and its derivative p21$^{H-ras}$ CVLL were produced in bacteria as described previously (19). Geranylgeranyl-cysteine (GG-Cys) and farnesyl-cysteine (F-Cys) were synthesized as described by Kamiya et al. (20) and purified by preparative TLC. All other solvents and chemicals were reagent grade and purchased from standard commercial sources.

General Synthetic Chemical Procedures. All reactions were conducted under dry argon, and stirred magnetically except as noted. Reaction temperatures refer to the external bath temperatures. All reactions and flash chromatography procedures were conducted under diminished light. Analytical TLC was performed on precoated (0.25 mm) silica gel 60F-254 plates purchased from E. Merck and developed with 30% ethyl acetate in hexane, except where noted otherwise. Preparative TLC was performed on precoated silica gel plates (E. Merck #13793-7) purchased from Alltech. Visualization was achieved either by UV irradiation, anisaldehyde-sulfuric acid spray followed by heating, or treating the plates with a 5% ethanolic phosphomolybdic acid solution followed by heating. Flash chromatography was performed on Merck silica gel 60 (230–400 mesh ASTM) purchased from VWR. All chromatographic solvents were purchased from VWR (E. M. Science—OMNISOLV High Purity Grade) and used as received. Anhydrous acetonitrile was purchased from Aldrich. Activated $MnO_2$ was purchased from Fluka; all other reagents were either purchased from Aldrich or Alfa Aesar, unless otherwise noted. IR spectra were recorded as liquid films using a NICOLET® 560 ESP FTIR spectrometer. NMR spectra were obtained in $CDCl_3$ (unless otherwise noted) at 200 MHz with a Varian XL200 spectrometer, or at 500 MHz with a Varian INOVA instrument. Chemical shifts for the following deuteriated solvents are reported in ppm downfield using the indicated reference peaks: $CDCl_3$ ($CDCl_3$ internal peak, 7.27 ppm for $^1$H, 77.4 ppm for $^{13}$C), $D_2O$ (TSP, 0 ppm), $C_6H_6$ ($C_6H_6$ internal peak, 7.37 ppm for $^1$H). Mass spectra were obtained with a Hewlett Packard 5890 Series II gas chromatograph with a 5972 series mass selective detector. Combustion analyses were performed by Atlantic Microlabs, Inc. Norcross, Ga.

(E,E)-3,7-Dimethyl-1-acetoxyl-2,6-octadien-8-al (5)

Geranyl acetate was oxidized as described previously with some modification (21). Forty milliliters (0.36 mol) of 90% tert-butyl hydroperoxide was added to a stirred suspension of 1.11 g (0.01 mol) of $SeO_2$, 1.4 g (0.01 mol) of salicylic acid, and 75 ml of $CH_2Cl_2$ in a 250 ml round bottom flask covered in aluminum foil. The resulting solution was allowed to stir to homogeneity at room temperature before being placed at 0° C. After ten minutes, 21.5 ml (0.10 mol) of geranyl acetate (4) was introduced dropwise. The mixture was stirred for 5 h at 0° C., and then for 20 h at rt. TLC analysis indicated the presence of starting material and two oxidized products ($R_f$ 0.38 aldehyde, $R_f$ 0.19 alcohol). The solution was diluted with 100 ml toluene, and solvents were removed under reduced pressure. The residue was then dissolved in toluene, washed with 5% $NaHCO_3$ to remove $H_2SeO_3$, saturated $CuSO_4$, saturated aqueous $Na_2S_2O_3$ (2×), water, brine, dried over $MgSO_4$ and filtered. The solvent was removed under reduced pressure affording a crude oil, which was dissolved in 100 ml dry $CH_2Cl_2$ and cooled to 0° C. 40.95 g (0.47 mol) of activated $MnO_2$ was added, and the suspension was stirred for 5 h at 0° C., then overnight at rt. The mixture was filtered over a short bed of Celite, and washed thoroughly with dry $CH_2Cl_2$. Solvent was evaporated under reduced pressure to yield a crude, pale yellow oil which was purified by flash chromatography on silica gel (5% EtOAc in hexane) affording 10.68 g (51 %) of 5 as a colorless oil; $^1$H NMR ($C_6H_6$, 200 MHz) δ9.47 (s, 1H), 5.98 (t, 1H, J=6.9 Hz), 5.48 (t, 1H, J=6.9 Hz), 4.75 (d, 2H, J=6.8 Hz), 2.11 (q, 2H, J=7.3 Hz), 1.92 (t, 2H, J=7.3 Hz), 1.91 (s, 3H), 1.79 (s, 6H), 1.59 (s, 3H); $^{13}$C NMR (50.3 MHz) δ195.47, 171.39, 153.70, 140.73, 140.08, 120.01, 61.48, 38.13, 27.33, 21.37, 16.77, 9.62.

(E,E)-8-Aniline-3,7-dimethyl-1-acetoxyl-2,6-octadiene (6)

The reductive amination procedure of Abdel-Magid et al. (22–25) was modified as follows. Into a 250 ml 3-neck flask covered in aluminum foil was introduced 150 ml of 1,2-dichloroethane, followed by 7.88 g (37.48 mmol) of 5, 3.76 ml (41.22 mmol) of fresh aniline, and 2.58 ml (44.89 mmol) of glacial acetic acid. After stirring for thirty seconds at room temperature, 11.12 g (52.47 mmol) of $NaBH(OAc)_3$ was added. The solution was stirred for 5 h at which time TLC analysis indicated no remaining starting material ($R_f$ of 6 0.46). The reaction mixture was quenched by pouring into a separatory funnel containing 200 ml of 5% $NaHCO_3$. The product was extracted with ether (3×75 ml), dried ($MgSO_4$), and concentrated to give a pale yellow, viscous oil. Purification by flash chromatography (10% EtOAc in hexane) yielded 9.15 g (85%) of a light-straw colored to colorless oil; $^1$H NMR (200 MHz) δ7.18 (m, 2H), 6.69 (m, 1H), 6.62 (m, 2H), 5.38 (m, 2H), 4.60 (d, 2H, J=7.2 Hz), 3.82 (s, 1H), 3.65 (s, 2H) 2.33–2.02 (m, 4H), 2.08 (s, 3H), 1.72 (s, 3H), 1.69

(s, 3H); $^{13}$C NMR (50.3 MHz) δ171.42, 148.84, 142.12, 133.13, 129.43, 125.71, 118.93, 117.44, 113.13, 61.68, 52.03, 39.50, 26.21, 21.37, 16.74, 15.00. IR: 3416, 3052, 3020, 2915, 2855, 1736, 1670, 1603, 1507, 1443, 1382, 1366, 1313, 1233, 1179, 1154, 1095, 1024, 992, 954, 868, 749, 693. LRMS (EI): m/z 287(M$^+$), 159 (2), 93 (7), 77 (2), 43 (2). Anal. Calcd for $C_{18}H_{25}NO_2$: C, 75.22; H, 8.77; N, 4.87. Found: C, 75.38; H, 8.63; N, 4.93.

(E,E)-8-Aniline-3,7-dimethyl-2,6-octadien-1-ol (7)

A 500 ml 3-neck flask covered in aluminum foil was charged with a solution of acetate 6 (8.00 g, 27.8 mmol) in 250 ml of methanol. Potassium carbonate (11.53 g, 83.4 mmol) dissolved in 20 ml of water was added, and the mixture was stirred at room temperature overnight. TLC analysis indicated complete hydrolysis to the alcohol 7 ($R_f$ 0.20). The mixture was then concentrated to ca. 100 ml on a rotary evaporator. Water was added (100 ml), and the mixture was extracted with four 100-mL portions of ether. The combined extracts were washed once with brine (100 ml), dried ($MgSO_4$), and concentrated to yield 6.48 g (95%) of 7 as a viscous, light-straw colored to colorless oil; $^1$H NMR (200 MHz) δ7.18 (m, 2H), 6.71 (m, 1H), 6.61 (m, 2H), 5.40 (m, 2H), 4.13 (d, 2H, J=6.9 Hz), 3.65 (s, 2H), 2.30–1.98 (m, 4H), 1.69 (s, 6H); $^{13}$C NMR (50.3 MHz) δ148.84, 139.45, 132.94, 129.45, 125.83, 124.09, 117.46, 113.18, 59.67, 52.01, 39.51, 26.24, 16.55, 15.04. IR: 3543, 3371, 3051, 3019, 2975, 2914, 2856, 1668, 1603, 1506, 1443, 1431, 1383, 1313, 1267, 1179, 1154, 1095, 992, 867, 749, 693. LRMS (EI): m/z 245(M$^+$), 159 (1), 146 (1), 93 (5), 77 (2), 41 (1), 29 (1). Purification by flash chromatography (30% EtOAc in hexane) yielded the analytical sample of 7. Anal. Calcd for $C_{16}H_{23}NO$: C, 78.32; H, 9.45; N, 5.71. Found: C, 78.13; H, 9.46; N, 5.88.

(E,E)-8-Aniline-1-chloro-3,7-dimethyl-2,6-octadiene (8)

The allylic chloride was synthesized as described for homoallylic alcohols by Sandri et al. (26) with some modification. Into a 25-mL pear shaped flask was added alcohol 7 (1.24 g, 5.05 mmol), N,N-diisopropylethylamine (1.41 ml, 8.09 mmol), and 12 ml of dry acetonitrile. The solution was stirred at 0° C. for 10 min. Solid dichlorotriphenylphosphorane (2.45 g, 7.58 mmol) was then added evenly to the reaction mixture over a 10 min period. After the final addition of $Ph_3PCl_2$, the reaction was allowed to stir at 0° C. for an additional hour, at which time TLC analysis ($R_f$ 0.62) indicated only the allylic chloride 8. The mixture was then loaded directly onto a silica gel column and purified by flash chromatography (hexane, then 5% EtOAc in hexane) to yield 1.00 g (75%) of pure chloride 8 as an unstable colorless oil which rapidly turned brown; $^1$H NMR (200 MHz) δ7.19 (m, 2H), 6.96 (m, 3 H), 5.31 (m, 2H), 4.02 (d, 2H, J=7.6 Hz), 3.68 (s, 2H), 2.18–1.86 (m, 4H), 1.69 (s, 3H), 1.63 (s, 3H); $^{13}$C NMR (50.3 MHz) δ145.47, 141.27, 133.67, 131.60, 129.38, 122.19, 120.86, 117.68, 55.25, 41.25, 38.89, 26.05, 16.20, 15.35.

(E,E)-8-Aniline-3,7-dimethyl-2,6-octadiene pyrophosphate (3)

The pyrophosphate was prepared as previously described (27,28). To a 50-mL glass centrifuge tube was added 7.45 g (7.6 mmol) of tris(tetrabutylammonium) hydrogen pyrophosphate. The flocculent white solid was dissolved in 20 ml of dry acetonitrile with vortexing. The milky white solution was then centrifuged at 2000 rpm for 10 min. The clear supernatant was decanted into a flame-dried, 100-mL, round-bottomed flask charged with 1.00 g (3.8 mmol) of chloride 8. The mixture was allowed to stir at room temperature for 2 hr. Solvent was removed and the pale yellow residue was dissolved in 3 ml of ion exchange buffer (ion exchange buffer was generated by dissolving ammonium bicarbonate (2.0 g, 25.3 mmol) in 1.0 L of 2% (v/v) isopropyl alcohol/water). Then, the resulting milky yellow solution was loaded onto a pre-equilibrated 2×30-cm column of Dowex AG 50W-X8 (100–200 mesh) cation exchange resin (ammonium form). The flask was washed twice with 5 ml of buffer and both washes were loaded onto the column before elution with 190 ml (two column volumes) of ion exchange buffer. The turbid yellow eluant was collected in a 600-mL freeze-drying flask, frozen, and lyophilized to yield 1.71 g of a cream-colored solid. The material was dissolved in 10 ml of 10:10:3 (v/v/v) chloroform:methanol:25 mM ammonium bicarbonate in a 50-mL glass centrifuge tube. The contents were mixed thoroughly on a vortex mixer, and the suspension was cleared by centrifugation for 10 min at 2000 rpm. The supernatant solution was removed with a pipette, the residue suspended in 10 ml of 10:10:3 (v/v/v) chloroform:methanol:25 mM ammonium bicarbonate, and the process repeated twice. The supernatant solutions were combined (30 ml total) and stored at –20° C. A TLC chamber was presaturated with 100 ml of 6:3:1 (v/v/v) isopropanol:concentrated ammonium hydroxide:water. Then, 1 ml of the chloroform:methanol:ammonium bicarbonate supernatant was loaded onto a 20 cm×20 cm×2 mm fluorescent silica preparative TLC plate and developed in the above solvent. The pyrophosphate was detected by short-wave UV light ($R_f$ 0.3–0.4). Notice: Do not expose pyrophosphate longer than necessary (1–2 seconds) as the compound is sensitive to short-wave UV light. The desired band was removed, extracted with 30 ml of 10:10:3 (v/v/v) chloroform:methanol:25 mM ammonium bicarbonate, and concentrated to yield 35 mg (1.05 g overall, 61%) of 3 as a light-cream colored solid; $^1$H NMR ($D_2O$, 200 MHz) δ7.28 (m, 2H), 6.88 (m, 3H), 5.42 (m, 2H), 4.47 (t, 2H, J=6.7 Hz), 3.69 (s, 2H), 2.25–2.01 (m, 4H), 1.69 (s, 3H), 1.64 (s, 3H); $^{13}$C NMR ($D_2O$, 50.3 MHz) δ148.74, 145.78, 135.54, 132.55, 129.83, 122.87, 122.22, 118.39, 65.78 (d, J=5.3 Hz), 54.41, 41.50, 28.29, 18.52, 16.73; $^{31}$P NMR ($D_2O$, 202.4 MHz) δ–6.87 (1P, d, J=22 Hz), –10.84 (1P, d, J=22 Hz). For increased solubility and ease of handling, the solid was dissolved in 25 mM ammonium bicarbonate, and converted to the sodium cation form by passage through a Dowex AG 50W-X8 cation exchange resin (100–200 mesh, Na$^+$). The column was eluted with 2% isopropyl alcohol/water and lyophilized to yield an off-white solid.

(E,E)-8-Aniline-3,7-dimethyl-2,6-octadiene-S-(N-tert-butoxycarbonyl-L-cysteine methyl ester) (11a)

The cysteine adduct was synthesized in an manner analogous to Brown et al. (29). The alcohol 7 (3.00 g, 12.2 mmol) was first converted into 8 as described above, but after stirring for 1 h, the solution was filtered directly through a short pad of silica gel (washing with 2% EtOAc in hexane). The heterogeneous solution was evaporated to a minimum volume (ca. 10 ml) and the resulting solution was added directly to 3.43 g (14.6 mmol) of N-tert-butoxycarbonyl-L-cysteine methyl ester (30) in 15 ml of a 2 M solution of ammonia in methanol. The solution was stirred at 0° C. for 3 hr and then overnight at room temperature. At this time, TLC analysis indicated that the majority of product present was 11a ($R_f$ 0.40). Solvent was removed under reduced pressure, the residue taken up in Et$_2$O, and washed with cold N HCl, 5% NaHCO$_3$, brine, and dried (MgSO$_4$). Flash chromatography eluting with 10% EtOAc in hexane afforded 3.69 g (65% from the alcohol 7) of a pale straw-colored oil; $^1$H NMR (200 MHz) δ7.18 (m, 2H), 6.65 (m, 3H), 5.39 (m, 2H), 5.21 (t, 1H, J=7.7 Hz), 4.54 (m, 1H), 3.76 (s, 3H), 3.64 (s, 2H), 3.18 (dd, 2H, J=4.5 Hz and 3.4 Hz), 2.89 (t, 2H, J=5.3), 2.31–1.94 (m, 4H), 1.68 (s, 6H), 1.47 (s, 9H); $^{13}$C NMR (50.3 MHz) δ172.11, 155.57, 148.91, 139.81, 133.04, 129.45, 125.78, 120.39, 117.40, 113.12, 80.37, 53.57, 52.73, 51.94, 39.49, 33.90, 30.25, 28.53, 26.28, 16.30, 14.93.

(E,E)-8-Aniline-3,7-dimethyl-2,6-octadiene-S-(N-tert-butoxycarbonyl-L-cysteine) (11b)

Ester 11a (1.64 g, 3.54 mmol) and K$_2$CO$_3$ (1.47 g, 10.6 mmol) were stirred in 20 ml MeOH:H$_2$O (20:1) overnight. Water (50 ml), was added to the mixture, and the solution was allowed to stir for an additional 15 min. The solution was diluted directly into a 500-mL separatory funnel containing 300 ml EtOAc and washed with cold 0.1 N HCl (2×100 mL). The aqueous washes were collected, and extracted once with 100 ml EtOAc. TLC analysis of 10b: R$_f$0.42, chloroform:methanol:acetic acid, 95:5:3. The organic extracts were collected, and washed once with acidic brine (10 ml N HCl in 100 ml brine). The solution was then dried (Na$_2$SO$_4$), filtered, and evaporated under reduced pressure to afford 1.54 g (97%) of 10b as a pale straw-colored oil (oxidizes readily in air); $^1$H NMR (200 MHz) δ8.31 (s, 2H), 7.20 (m, 2H), 6.79 (m, 3H), 5.41 (m, 2H), 5.18 (t, 1H, J=6.9 Hz), 4.47 (m, 1H), 3.67 (s, 2H), 3.16 (m, 2H), 2.89 (m, 2H), 2.23–1.92 (m, 4H), 1.64 (s, 6H), 1.47 (s, 9H); $^{13}$C NMR (50.3 MHz) δ175.48, 155.92, 146.26, 139.41, 131.59, 129.62, 127.84, 120.73, 120.07, 115.54, 80.47, 53.68, 39.24, 33.86, 30.20, 29.35, 28.57, 26.21, 16.31, 15.13.

(E,E)-8-Aniline-3,7-dimethyl-2,6-octadiene-S-L-cysteine (11c)

Compound 11b (1.00 g, 2.23 mmol) was dissolved in 5 ml of CH$_2$Cl$_2$ in a 50-mL pear shaped flask. Then, 50 ml of a 1 N HCl solution in Et$_2$O were added. The resulting mixture was stirred rapidly, became cloudy, and allowed to stir overnight. The solution and precipitate were then placed at −80° C. overnight and filtered on a sintered glass funnel. Filtration of the precipitate gave 11c as a cream-colored solid. TLC analysis of the zwitterion form of 11c indicated only one product (R$_f$0.5; CH$_3$CN:H$_2$O, 4:1, ninhydrin positive). The solid began to gel on the funnel, and the material was immediately dried in vacuo (50° C., 0.5 mmHg) to afford 0.67 g (68%) of 11c as a hygroscopic light-cream colored solid; $^1$H NMR (D$_2$O, 200 MHz) δ7.65–7.36 (m, 5H), 5.43 (m, 1H), 5.10 (m, 1H), 4.27–4.04 (m, 2H), 3.97 (s, 2H), 3.35–2.86 (m, 4H), 2.77–2.49 (m, 1H), 2.33–1.80 (m, 4H), 1.75 (s, 3H), 1.61 (s, 3H); $^{13}$C NMR (D$_2$O, 50.3 MHz) δ174.45, 143.85, 139.55, 136.90, 133.31, 132.97, 127.84, 127.93, 126.03, 122.38, 62.68, 55.77, 40.70, 33.52, 31.69, 28.56, 18.14, 17.17. Anal. Calcd for C$_{19}$H$_{30}$Cl$_2$N$_2$O$_2$S.H$_2$O: C, 51.93; H, 7.34; N, 6.37. Found: C, 51.50; H, 7.11; N, 6.10.

Production of Recombinant CAAX GGTase-1 and FTase in Sf9 Cells—Recombinant FTase was prepared by coinfection of fall army worm ovarian (Sf9) cells with recombinant baculoviruses encoding the α- and β-subunits of rat FTase and purified as previously described (19). The FTase α-subunit had been modified to contain a 6×Histidine affinity tag at its N-terminus to allow rapid purification using Ni$^{2+}$-Sepharose affinity chromatography as described (10). Recombinant CAAX GGTase-1, a heterodimer of the α-subunit of FTase and the β-subunit of CAAX GGTase-1, was produced as follows. A cDNA clone that encodes the GGTase-1 β-subunit was kindly provided by Dr. Guy James (University of Texas, Southwestern Medical Center, Dallas). A PstI-EcoRI fragment that contains the GGTase-1 β-subunit was ligated into a PstI-EcoRI digested pVL-1392 baculovirus transfer vector (10) and designated pVL-GGTB. Recombinant baculoviruses encoding the GGTase-1 β-subunit were generated by cotransfection of Sf9 cells with pVL-GGTB and linear BacPAK6 viral DNA (Clontech) and plaque purified as described (10). To produce recombinant CAAX GGTase-1, Sf9 cells (100 ml in suspension at 1×10$^6$ cells/ml) were grown as previously described and infected with recombinant baculoviruses encoding the α-subunit of FTase and the β-subunit of GGTase-1 at a multiplicity of infection of 1 α-subunit and 1 β-subunit encoding virus per cell. Twenty-four hours after infection, the cells were collected and washed once with ice-cold phosphate-buffered saline. Cells were lysed in 10 ml of buffer containing 50 mM Tris-HCl (pH 7.4), 50 µM ZnCl$_2$, 1 mM dithiothreitol, 1 mM phenylmethylsulfonyl fluoride, 5 mg/ml pepstatin, 5 mg/ml leupeptin, and 5 mg/ml aprotinin and treated in a Parr cell disruption bomb. The lysate was then centrifuged at 10$^5$×g for 1 hr at 4° C., and the supernatant was chromatographed on a Ni$^{2+}$-Sepharose column.

Assay for Farnesyltransferase Activity—Farnesyltransferase activity was assayed by measuring the amount of [$^3$H]farnesyl or [$^3$H]anilinogeranyl transferred from [$^3$H]FPP or [$^3$H]AGPP to recombinant p21$^{H\text{-}ras}$, as described previously (31). Unless otherwise stated, each reaction mixture contained the following components in a final volume of 25 µl: 50 mM Tris (pH 7.4), 20 mM KCl, 0.2% octyl β-glucopyranoside, 1 mM dithiothreitol, 10–20 ng recombinant FTase, 5 µM p21$^{Ha\text{-}ras}$, 3 mM MgCl$_2$, 50 µM ZnCl$_2$, and 0.6 µM [$^3$H]FPP (33,000 dpm/pmol; American Radiochemical Co.) or 0.1–5 µM [$^3$H]AGPP (37,400 dpm/pmol). Following incubation for the indicated times at 37° C., the amount of [$^3$H]prenyl transferred was measured by ethanol-HCl precipitation and filtration on glass fiber filters with modification as previously described (19). A blank value was determined in parallel incubation mixtures containing no enzyme. This blank value was subtracted from each reaction before calculating pmol [$^3$H]prenyl transferred.

Assay for CAAX Geranylgeranyltransferase-1 Activity—CAAX geranylgeranyltransferase activity was assayed by measuring the amount of [$^3$H]geranylgeranyl transferred from [$^3$H]GGPP to recombinant p21$^{H\text{-}ras}$ CVLL, as described previously (32). Unless otherwise stated, each reaction contained the following components in a final volume of 25 µl: 50 mM Tris-HCl (pH 7.4), 5 mM dithiothreitol, 20 µM Zwittergent (3–14), 1 µM [$^3$H]GGPP (33,000 dpm/pmol; American Radiochemical Co.), 5 µM p21$^{H\text{-}ras}$ CVLL, 5 µM ZnCl$_2$, 5 mM MgCl$_2$, 100 ng recombinant CAAX GGTase-1, and the indicated amount of unlabeled AGPP. Following incubation at 37° C. for 15 min, the amount of [$^3$H]geranylgeranyl transferred was measured by ethanol-HCl precipitation followed by filtration on glass fiber filters. A blank value was determined in parallel incubation mixtures containing no enzyme and was subtracted from each reaction.

Assay for Squalene Synthase Activity—Initial rates of squalene synthase activity present in bovine brain microsome fractions were assayed as previously described

(19) with minor modifications. Typical reaction mixtures contained crude bovine brain microsomes (0.2 mg membrane protein), 55 mM HEPES (pH 7.4), 5.5 mM $MgCl_2$, 11 mM KF, 1 mM NADPH, and 0.05 mM [$^3$H]FPP (105 cpm/pmol) in a total volume of 100 μl. Unlabeled AGPP and FPP were added at the indicated concentrations. Assay mixtures were incubated for 30 min at 37° C., and the reactions terminated by the addition of 50 μl of 40% (wt/vol) KOH and then 100 μl of 95% ethanol. The resulting mixtures were incubated at 60° C. for 2 h and then cooled to room temperature. Authentic carrier squalene (20 μg) was added to each reaction tube, which were then extracted three times with petroleum ether. The lipid extracts were pooled, washed with water three times, and evaporated under a stream of $N_2$. The lipid residue was redissolved in 100 μl $CHCl_3/CH_3OH$ (2:1 vol/vol) and an aliquot (30 μl) was taken to determine the amount of labeled lipid formed by scintillation spectrometry. The remaining sample was analyzed on Silica gel G 60 TLC plates by developing with hexane (33). In all analyses the squalene standard was located by anisaldehyde spray reagent (34), and radioactive zones were located with a Bioscan Imaging System 200-IBM.

Results

Design and Synthesis of AGPP. We conceptually composed AGPP by replacing the terminal isoprene of FPP with an aniline functionality (FIG. 1). The synthesis of AGPP was accomplished in five steps from commercially available geranyl acetate as illustrated in Scheme 1 and described in detail in the experimental section. The key step in the synthesis of AGPP was the reductive amination of the aniline by the geranyl α-β unsaturated aldehyde with NaBH $(OAc)_3$ to form the lipid portion of the analog. The presence of the amine precluded the implementation of standard methods (35–37) to convert the lipid alcohol to the pyrophosphate via an activated chloride intermediate. The published procedure that converted homoallylic alcohols into the corresponding bromides using dibromotriphenylphosphorane (26) was modified by using dichlorotriphenylphosphorane to convert the alcohol to the chloride, which was then immediately converted to the pyrophosphate, AGPP.

Figure 2:
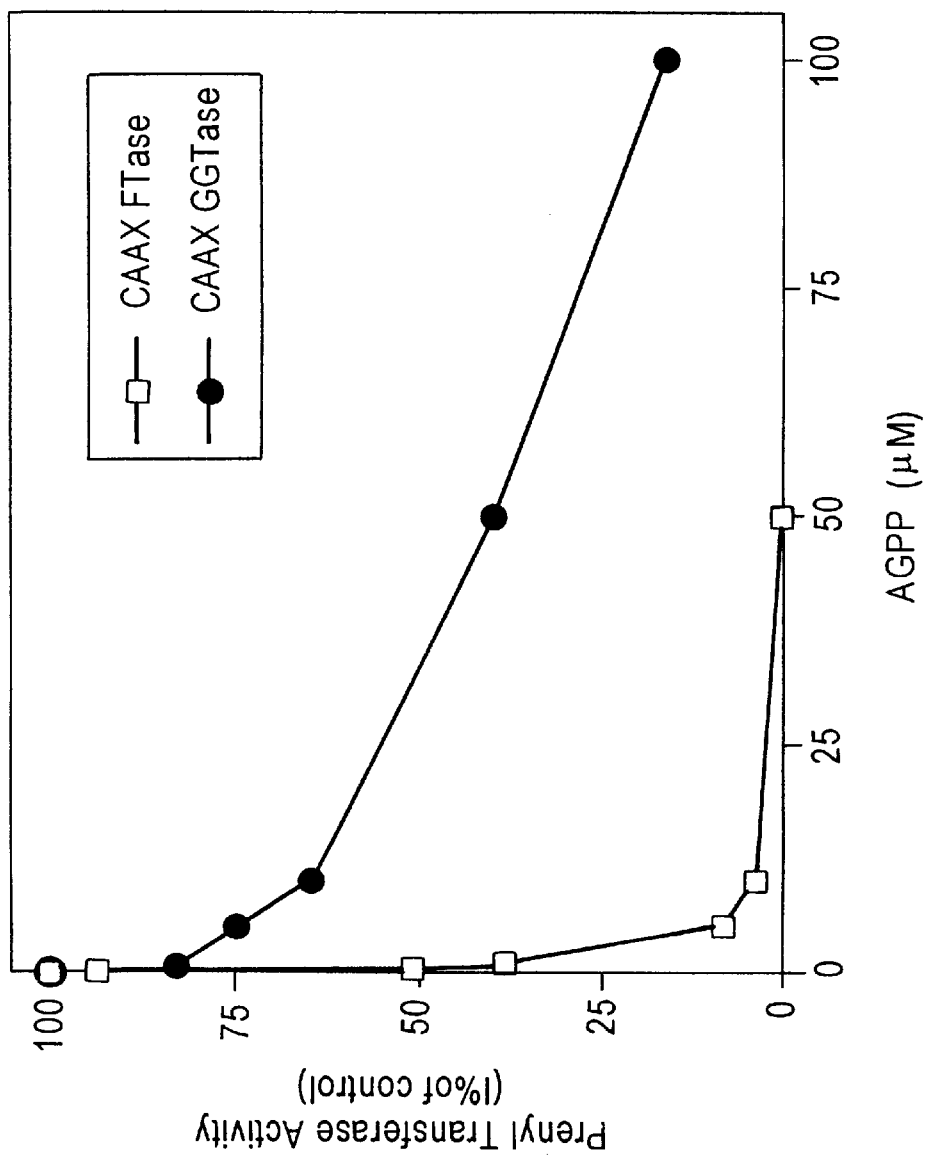
FIG. 2. Differential Inhibition of Farnesyltransferase and CAAX Geranylgeranyltransferase by AGPP. The assay mixtures contained (in a final volume of 25 μl) various components as described in "Experimental Procedures". After incubation for 15 min at 37° C., the amount of [$^3$H]prenyl group transferred to the appropriate protein substrate [H-Ras (CVLS) for FTase and H-Ras (CVLL) for CAAX GGTase] was measured by precipitation with ethanol-HCl. The assays contained 10 ng recombinant rat FTase, 5 μM H-Ras, and 0.6 μM [$^3$H]FPP (33,000 dpm/pmol) or 100 ng recombinant rat CAAX GGTase, 5 μM H-Ras CVLL, and 1 μM [$^3$H]GGPP (33,000 dpm/pmol) and the indicated concentration of unlabeled AGPP. The 100% of control values were 1.1 and 5.5 pmol of [$^3$H]farnesyl or [$^3$H]geranylgeranyl transferred per tube. Each value is the average of duplicate incubations and is representative of two separate experiments.
Figure 3:
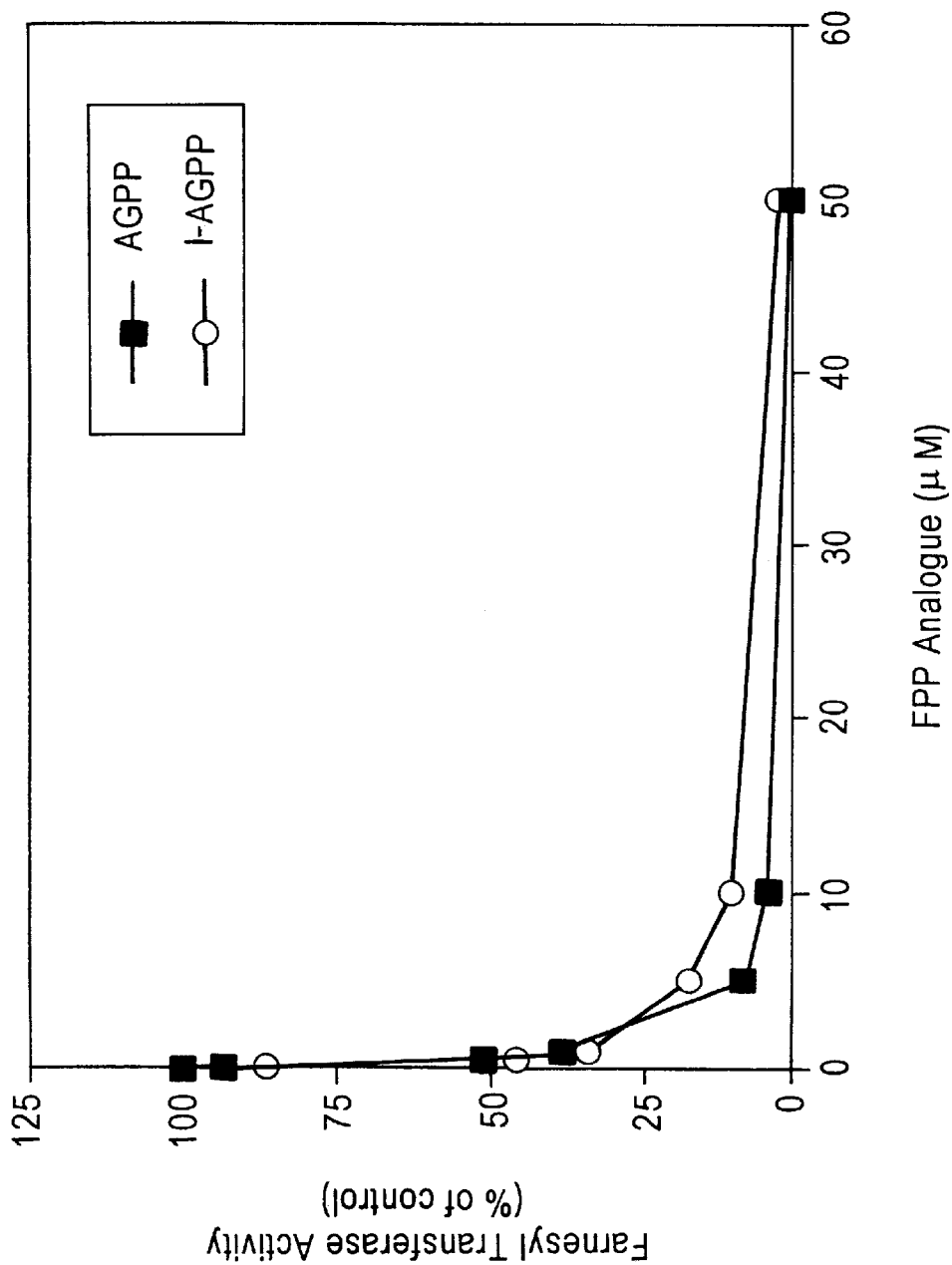
FIG. 3. Inhibition of Farnesyltransferase by AGPP and I-AGPP. The enzymatic activity was measured in the presence of the various concentrations of either AGPP or I-AGPP as described in FIG. 3. The 100% control values were 1.9 and 2 pmol. Each value is the average of duplicate incubations and is representative of three separate experiments.

Inhibition of Farnesyltransferase by AGPP—AGPP was tested for its ability to inhibit recombinant rat brain FTase activity in vitro. AGPP inhibited FTase in a concentration dependent manner with an $IC_{50}$ value of 0.6 μM (FIG. 2). In additional experiments, unlabeled AGPP and unlabeled FPP competed at essentially the same concentrations in this reaction (data not shown). The inhibition was not overcome by altering either the $MgCl_2$ or $ZnCl_2$ concentrations in the assay (data not shown), indicating that the inhibition was not due to the sequestration of divalent cations by AGPP. The modification of the aniline ring at the para position by iodination did not alter its ability to inhibit FTase activity in vitro (FIG. 3). Moreover, the anilinogeranyl alcohol (AG-OH) at concentrations as high as 250 μM did not significantly inhibit this reaction (data not shown), suggesting that while the aniline ring structure can be modified without altering FTase inhibition, the pyrophosphate moiety is critical for inhibition.

Kinetic analyses were carried out to investigate the mechanism of FTase inhibition by AGPP. Double reciprocal plots of the rate of FTase-catalyzed farnesylation of recombinant Ha-Ras-CVLS at various concentrations of [$^3$H]FPP and AGPP and a constant concentration of Ras, showed that the addition of AGPP changed the $K_m$ value for FPP but does not alter the $V_{max}$, consistent with competitive inhibition with respect to FPP (data not shown). In contrast, AGPP did not apparently affect the $K_m$ value for the substrate protein Ha-Ras. The same $K_m$ value was observed when the Lineweaver-Burke plot was analyzed under different Ras and AGPP concentrations in the presence of a constant concentration of FPP. Thus, AGPP appears to act as a competitive inhibitor of FTase with respect to FPP and a noncompetitive inhibitor with respect to Ha-Ras protein. AGPP inhibition is reversible, since transfer of [$^3$H]-FPP by FTase to Ras was restored by isolating the farnesyltransferase by gel filtration chromatography after preincubation in the presence of 50 μM AGPP (data not shown).

To evaluate the selectivity of AGPP inhibition, we examined its inhibitory activity against recombinant GGTase I, as measured by incorporation of radioactivity from [$^3$H] geranylgeranylpyrophosphate into Ha-Ras-CVLL. GGTase I catalyzes the transfer of a geranylgeranyl isoprene to proteins having a C-terminal CAAX sequence in which X is a leucine (2). As expected for an FPP analogue (32), AGPP inhibits GGTase I activity much less efficiently than it does FTase (FIG. 2). The $IC_{50}$ value for GGTase I inhibition is 31 μM, and approximately 20% of the GGTase I activity remains at AGPP concentrations of greater than 100 μM. AGPP is a 50 fold better inhibitor of FTase than GGTase I.

[$^3$H]AGPP is a Substrate for Farnesyltransferase in vitro

Figure 4A:
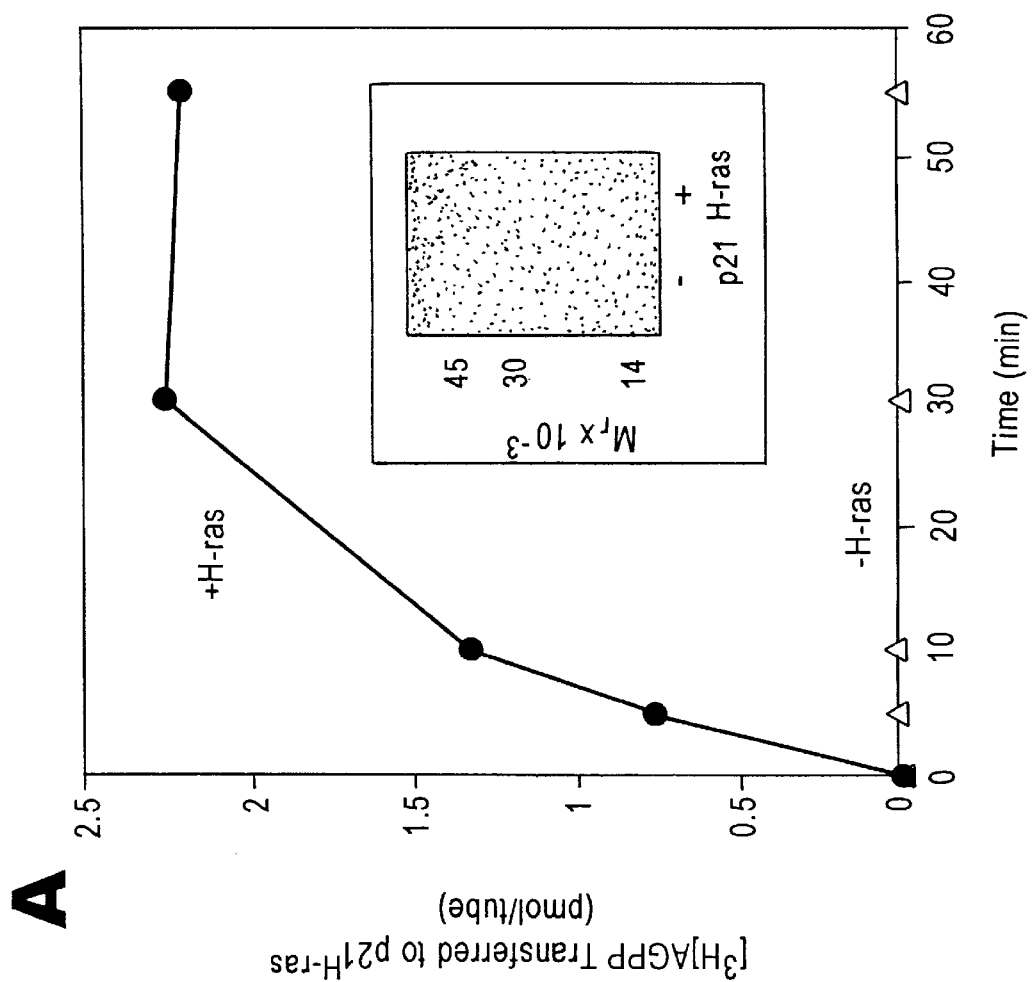
FIG. 4. Transfer of Anilinogeranyl from [$^3$H]AGPP to p21$^{Ha-ras}$ by Farnesyltransferase. (A) Each reaction contained 1 µM [$^3$H]AGPP (37,400 dpm/pmol) and 10 ng of recombinant FTase in the absence (triangles) or presence (circles) of 5 µM p21$^{Ha-ras}$ Duplicate samples were incubated for the indicated times at 37° C., and ethanol-HCl precipitated radioactivity was measures as described under "Experimental Procedures". The inset shows the migration of on a 12.5% SDS-polyacrylamide gel of an aliquot from the reaction carried out for 1 hr in the presence (+) or absence (−) of p21$^{Ha-ras}$. The gel was treated with Amplify solution (Amersham), dried, and exposed to Kodak X-OMAT AR film for 2 days at −70° C. The migration of molecular weight markers placed in a adjacent lane is shown. (B) The AGPP substrate saturation curve for FTase was determined by varying the amount of [$^3$H]AGPP in the standard reaction described above. Assays were carried out in duplicate for 30 min at 37° C., and the ethanol-HCl precipitable radioactivity measured. The data is representative of three independent experiments.
Figure 4B:
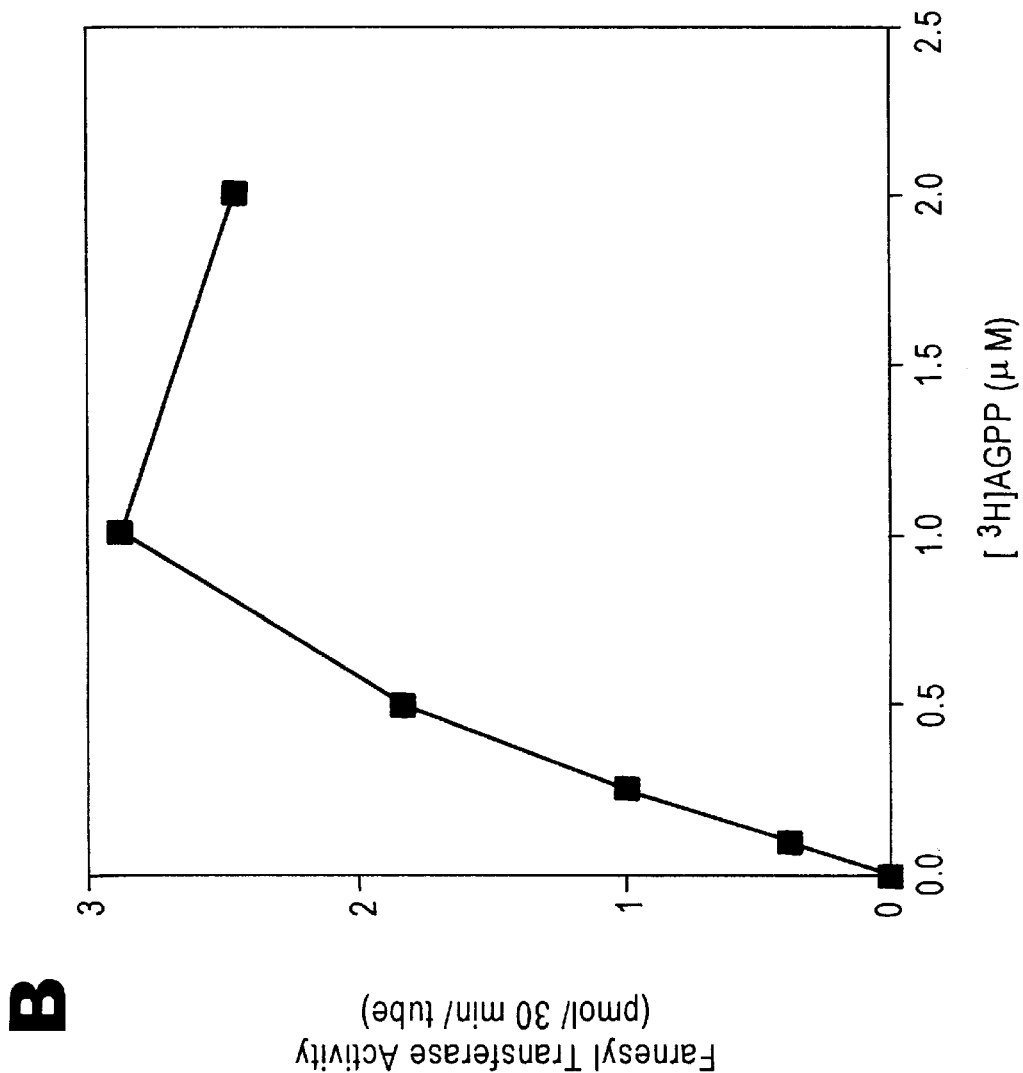
Figure 5:
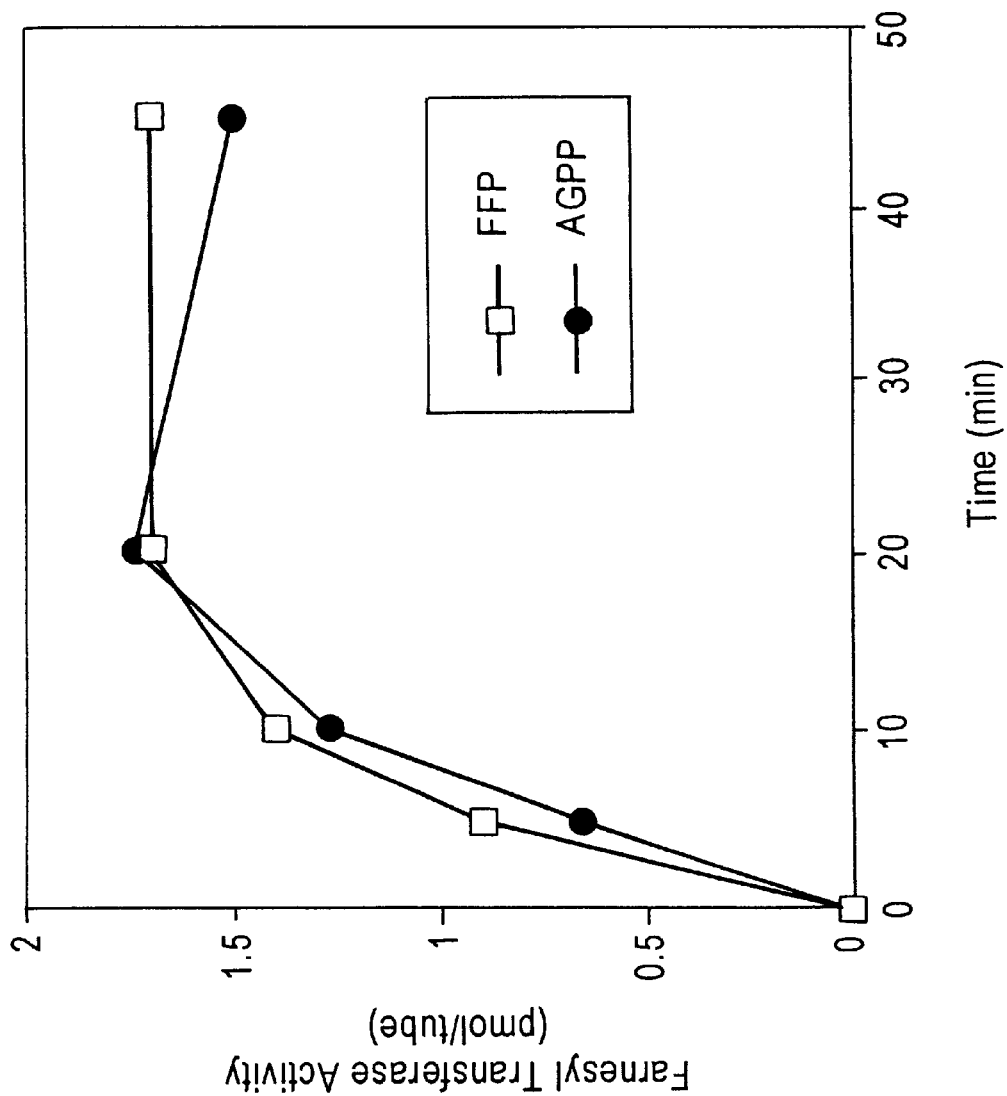
FIG. 5. [$^3$H]AGPP and [$^3$H]FPP are Bound and Transferred with Comparable Affinities by Farnesyltransferase. Farnesyltransferase (10 ng) was incubated in a final volume of 25 µl in the presence of 1.0 µM [$^3$H]AGPP or [$^3$H]FPP and 5 µM wild-type p21$^{Ha-ras}$. After incubation for 30 min at 37° C., the amount of [$^3$H]prenyl transferred to p21$^{Ha-ras}$ was determined as described under "Experimental Procedures". Each value is the average of duplicate incubations and is representative of five separate experiments.

The observed inhibition kinetics could be a manifestation of the ability of AGPP to act as an alternative substrate for FTase. To evaluate the potential of AGPP to serve as a substrate of FTase, [$^3$H]-AGPP was prepared by a similar route as described above, incorporating tritium with a specific activity of 17 Ci/mmol (synthesis to be reported elsewhere). FIG. 4A shows that FTase incorporated radioactivity from [$^3$H]AGPP into p21$^{H-ras}$ in a time dependent fashion at 37° C. The incorporated radioactivity was detected as a band of the expected molecular weight of farnesylated p21$^{H-ras}$ on SDS-polyacrylamide gels (FIG. 4A, inset). Transfer of [$^3$H]AGPP required an intact CVLS sequence, since recombinant p21$^{H-ras}$ in which this motif was removed eliminated the incorporation of tritium into the protein by [$^3$H]AGPP (data not shown). The concentration of [$^3$H]AGPP that gave half-maximal reaction velocity was approximately 0.5 μM (FIG. 4B). This saturation curve was almost identical to that obtained with [$^3$H]FPP, suggesting that FTase has a similar affinity for AGPP and FPP. FIG. 5 shows that FTase transfers [$^3$H]AGPP and [$^3$H]FPP (both at 1 μM) to p21$^{H-ras}$ with similar rates. Either non-radiolabeled AGPP or FPP, but not AG-OH or farnesol were found to inhibit the time and concentration dependent transfer of [$^3$H]AGPP to p21$^{H-ras}$ (data not shown).

Figure 6:
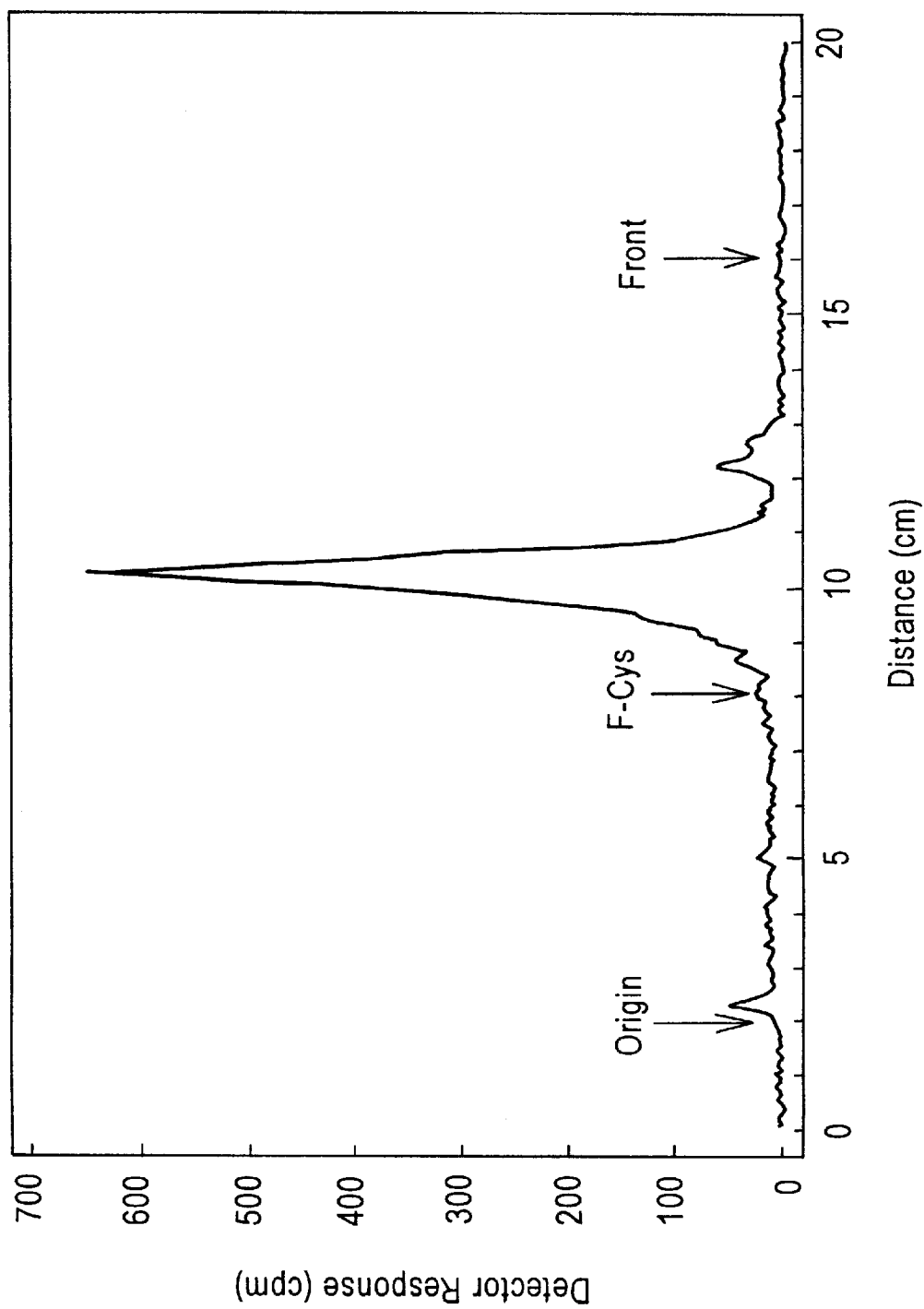
FIG. 6. Identification of [$^3$H]AGPP-Derived Radioactive Material Transferred to p21$^{Ha-ras}$. An aliquot from a standard FTase reaction was subjected to Pronase E digestion as described under "Experimental Procedures". The labeled products, extracted with 1-butanol, were analyzed on C18 reverse-phase TLC plates developed in acetonitrile:water:acetic acid (75:25:1). Radioactive zones were located with a Bioscan Imaging System 200-IBM. The arrows indicate the position of authentic F-Cys, GG-Cys, and AG-Cys. O and F denote the positions of the origin and solvent front. The data shown are representative of two independent experiments.

To verify that p21$^{H-ras}$ was radiolabeled by the transfer of the [$^3$H]AG group from [$^3$H]AGPP to a cysteine residue, radiolabeled p21$^{H-ras}$ was digested with Pronase E, and the butanol-soluble products analyzed by reverse phase chromatography. The analysis depicted in FIG. 6 shows that a major product, with a chromatographic mobility consistent with authentic AG-cysteine, the expected product of appropriate transfer of AGPP to Ras, is liberated from the labeled protein by the proteolysis.

We also tested whether I-AGPP served as a substrate for FTase. $^{125}$I-AGPP was synthesized from carrier free Na$^{125}$I and iodobeads (Pierce). FTase incorporated radioactivity from the $^{125}$I-AGPP into p21$^{H-ras}$ in a time and substrate dependent manner similar to [$^3$H]AGPP (data not shown). The incorporated radioactivity was detected as a single band which comigrated with authentic prenylated p21$^{H-ras}$ on SDS-polyacrylamide gels as described above (see FIG. 4A).

AGPP does not Inhibit Squalene Synthase Activity

Figure 7:
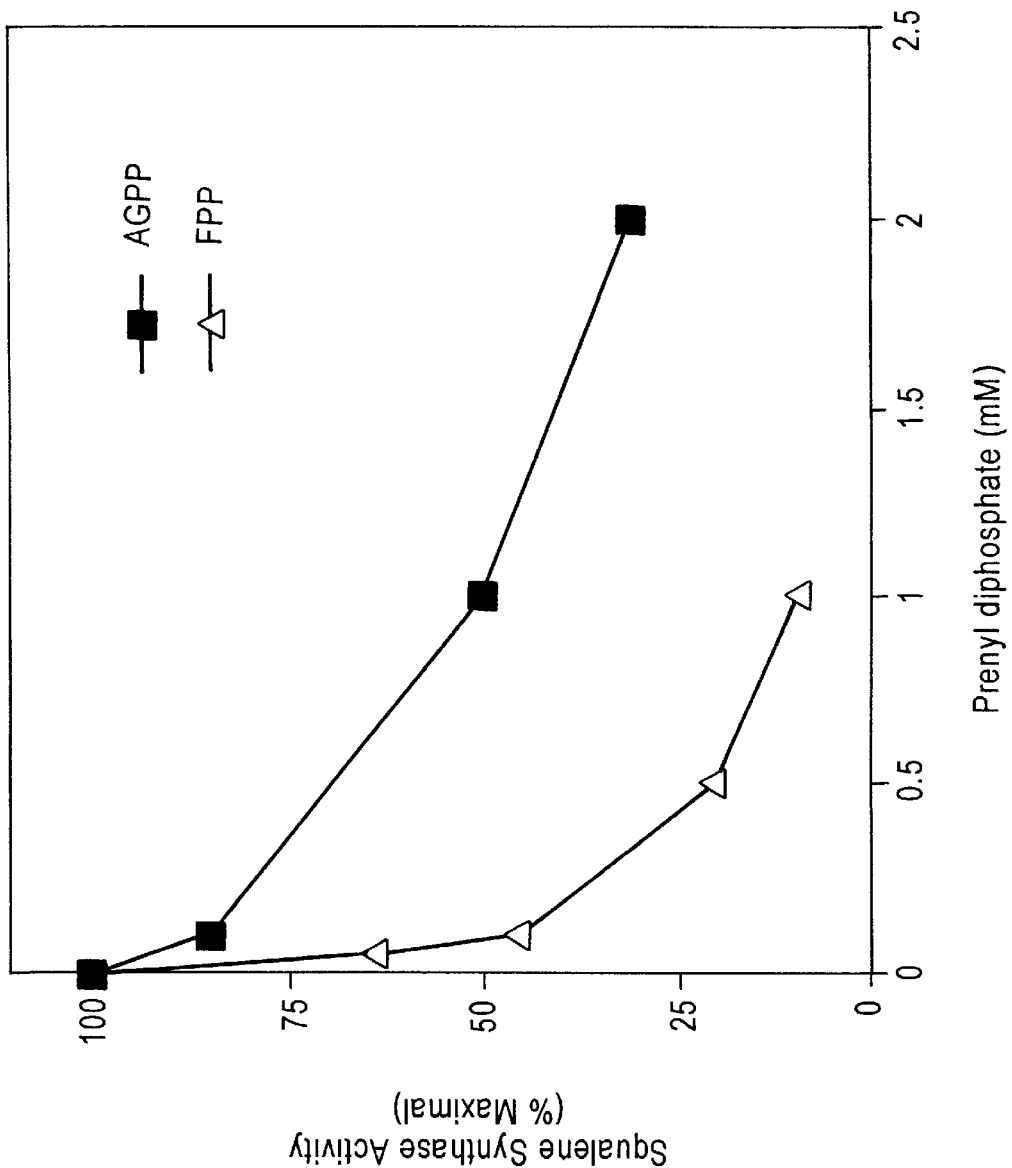
FIG. 7. Inhibition of Squalene Synthase by AGPP. The initial rates of squalene synthase activity were determined from bovine brain microsomal preparations in the presence of the indicated concentration of unlabeled AGPP (filled squares) or unlabeled FPP (open triangles) under the in vitro conditions described in "Experimental Procedures." Crude bovine brain microsomes and 0.05 mM [$^3$H]FPP (105 cpm/pmol) and unlabeled AGPP and FPP were added at the indicated concentrations and incubated for 30 min. at 37° C. The reactions were terminated with 40% (wt/vol) KOH and 95% ethanol. Authentic carrier squalene (20 µg) was added and the reactions extracted with petroleum ether. The amount of labeled lipid formed was measured by scintillation counting. Each value is the average of duplicate incubations and is representative of three separate experiments.

Some of the previously characterized FTase inhibitors, particularly those competitive for FPP binding, have been described as inhibitors of squalene synthase, an enzyme that utilizes FPP and is an important secondary regulatory protein in the cholesterol biosynthetic pathway (38). AGPP was found to be a far less potent in vitro inhibitor of squalene synthase activity than FPP (FIG. 7). Studies conducted with [$^3$H]AGPP aimed at detecting conversion of the analog to organic soluble products resulting from coupling reactions showed no activity (data not shown).

Transfer of FPP Analog AGPP to Ras by Farnesyltransferase in vitro

Biochemical and biological properties of the prototypical analog AGPP have been characterized.

FIG. 5 depicts transfer of unnatural anilinogeranyl lipid from [$^3$H]AGPP and transfer of farnesyl lipid from [$^3$H]FPP to H-Ras by FTase. Farnesyltransferase (10 ng) was incubated in a final volume of 25 µl in the presence of 1.0 µM [$^3$H]AGPP or [$^3$H]FPP and 5 µM wild-type H-Ras. After incubation for 30 min. at 37° C., the amount of [$^3$H]prenyl transferred to H-Ras was determined by ethanol-HCl precipitation and scintillation counting. Each value is the average of duplicate incubations and is representative of five separate experiments.

FIG. 2 shows that AGPP differentially inhibits transfer of FPP to H-Ras by FTase and transfer of GGPP to H-Ras-CVLL by GGTase I. After incubation for 15 min. at 37° C., the amount of [$^3$H]prenyl group transferred to the appropriate protein substrate [H-Ras (CVLS) for FTase and H-Ras (CVLL) for CAAX GGTase] was measured by precipitation with ethanol-HCl. The assays contained 10 ng recombinant rat FTase, 5 µM H-Ras, and 0.6 µM [$^3$H]FPP (33,000 dpm/pmol) or 100 ng recombinant rat CAAX GGTase, 5 µM H-Ras CVLL, and 1 µM [$^3$H]GGPP (33,000 dpm/pmol) and the indicated concentration of unlabeled AGPP. The 100% of control values were 1.1 and 5.5 pmol of [$^3$H]farnesyl or [$^3$H]geranylgeranyl transferred per tube.

It has thus been shown that [$^3$H]AGPP is transferred appropriately to p21$^{H\text{-}Ras}$ by FTase and that 0.5 µM [$^3$H] AGPP gives a half-maximal reaction velocity. (See FIG. 5). (See references 9, 28, 29, infra). This transfer curve was almost identical to that obtained with [$^3$H]FPP, suggesting that FTase has a similar affinity for AGPP and FPP. [$^3$H] AG-cysteine 11 is the expected product of appropriate transfer of AGPP to p21$^{H\text{-}Ras}$. It has been further shown that [$^3$H]AG-cysteine is found to be the major radiolabeled product from p21$^{H\text{-}Ras}$ modified by [$^3$H]AGPP and FTase after complete digestion of the modified protein with Pronase E (data not shown) (76). This assay suggests that derivatives of FPP can be synthesized that are competitive inhibitors which do not adversely affect subsequent target protein binding and are appropriately transferred.

Inhibition of FTase and GGTase I by AGPP. To evaluate the selectivity of AGPP inhibition, its inhibitory activity against recombinant GGTase I was determined, as measured by incorporation of radioactivity from [$^3$H] geranylgeranylpyrophosphate to H-Ras-CVLL. (See FIG. 2) (See reference 77, infra). As expected for an FPP analogue (32), AGPP inhibits GGTase I activity with a 50 fold lower efficiently than it does FTase with an IC$_{50}$ value for GGTase I inhibition of 31 µM. The selectivity shown by AGPP in this assay suggests that replacing the terminal isoprene unit of FPP with an anilino function gives molecules that can be effectively discriminated against by GGTase I while retaining activity against FTase. However, [$^3$H]AGPP is transferred by GGTase I to H-Ras-CVLL with a low efficiency, indicating that AGPP is a prototype molecule for additional analogs that may be more selective for GGTase I.

Figure 8:
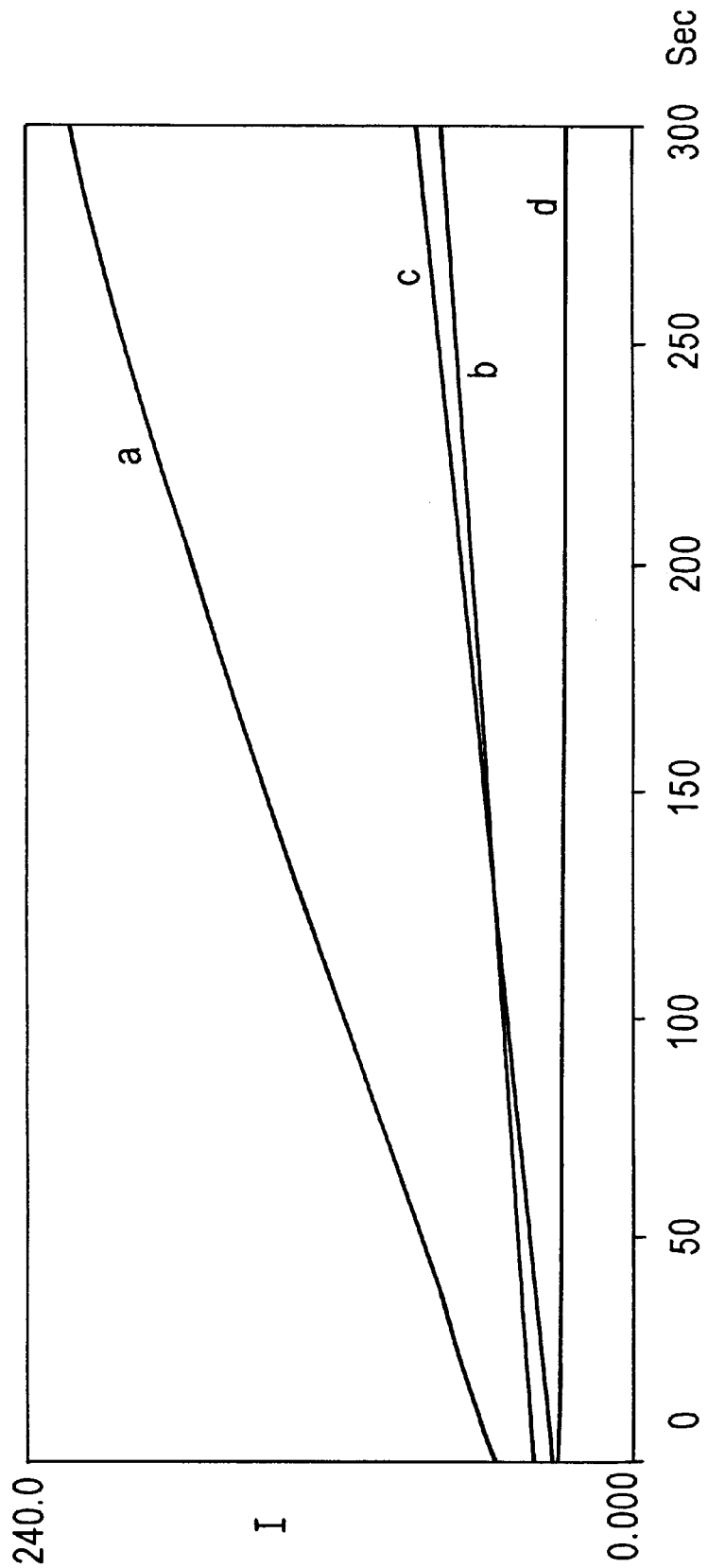
FIG. 8. Progress Curves for Transfer of FPP and Analog Pyrophosphates to Dansyl-GCVLS by FTase. The reaction is monitored for fluorescence intensity at 505 nm with excitation at 340 nm. (a) FPP, (b) AGPP, (c) 8-(pentafluoroaniline)geranyl pyrophosphate, (d) blank.

Continuous Fluorescence Assay for Analog Transfer: An important requirement for these studies is the development of a rapid technique for evaluating whether FPP analogs that are efficiently and appropriately transferred to target substrates by FTase. The analogs were evaluated for their ability to be transferred by FTase to the pentapeptide N-dansyl-GCVLS in a continuous fluorescence assay. (See references 78, 79, infra). There is a time dependent increase in the fluorescence of the dansyl group due to the local increase in hydrophobicity as the adjacent cysteine residue is isoprenylated. Time-dependent increases in the fluorescence of the dansyl group for analogs 1, 2, 4 and 12 (see table 1) are apparent, but the magnitude and rate of increase in fluorescence is not identical to FPP. (FIG. 8). The photoreactive analogs 5 and 6 show no increase in fluorescence, and are not transferred. The diminished fluorescence intensity relative to farnesyl for the analogs that are transferred is possibly due to two factors: 1) the analog is being transfer with a lower efficiency and 2) the analog does not enhance the fluorescence of dansyl group as well as FPP.

FIG. 5 depicts the progress curves for transfer of FPP and analog pyrophosphates to dansyl-GCVLS by FTase. The reaction is monitored for fluorescence intensity at 505 nm with excitation at 340 nm. (a) FPP (b) 1 (c) 4 (d) blank.

The fluorescence enhancement for farnesyl is 14 fold and for the untransferrable analog ω-benzophenone-geranyl it is 2.8 fold. Both of these effects may be occurring simultaneously and have been observed in other systems. (See reference 68, infra). Studies with [$^3$H]-AGPP suggest that he kinetics of transfer are identical to those of FPP. Therefore, the decrease in fluorescence enhancement observed upon modification of dansyl peptide by AGPP relative to FPP is most likely due to a lower enhancement of the fluorescence, not slower transfer. Comparison of the structures of the analogs tested permit making an initial approach to a SAR for transfer by FTase. This analysis suggests that a molecular ruler for lipid pyrophosphate substrate discrimination is operating. The longest analogs are 5 and 6 due to the linear three atom p-azido moiety on the aniline ring and may not fit in the lipid binding cleft of FTase in a productive way, much like GGPP. AGPP is very close in size to FPP, and is transferred efficiently. Surprisingly, changing the electronic properties of AGPP by perfluorination to give 4 does not change the apparent kinetics of transfer. Analogs with p-iodo and p-nitro substituents are transferred. This assay allows rapid screening of analogs as they are synthesized for their ability to be transferred by FTase to protein substrate, the first and obligatory step in Ras post-translational maturation. These results provide crucial evidence that additional structural modifications can be made to the AGPP skeleton that will yield functional, transferable molecules essential for achieving the purposes of the invention. Groups that are either inefficiently or not transferred are useful as potential FTIs. Such potential is illustrated in the experiments outlined below.

AGPP can functionally substitute for FPP in *Xenopus laevis* oocyte maturation assays. Most of what is known regarding the role of post-translational lipidation for the function of a lipidated protein in the context of a living cell comes from genetic approaches. This experimental strategy consists of introducing mutations to a given protein, which either adds or removes lipidation sites, and comparison of its function to the wild-type protein either by microinjection or by overexpression of the mutant gene in transfected cell lines. Although this approach has established that lipidation is essential for Ras function, the contribution of individual lipids to the overall biology of Ras and the role of their exact chemical structure for signaling has not been forthcoming. In addition, the lack of suitable reagents (such as specific inhibitors of protein palmitoylation, CaaX proteolysis, or methylation) has not allowed the functional role of these processes to be directly addressed. Finally, although transfection studies can provide qualitative information, they do not readily reveal the quantitative contribution of individual processing steps to Ras function. In these transfection studies Ras is typically overexpressed at levels much higher than those present in normal cells, and the contribution of a particular lipid modification to the overall biological activity of Ras may be underestimated.

Recently, a novel methodology involving the microinjection of known amounts of Ras into Xenopus oocytes has been described (see references 24, 45, infra), thereby permitting a quantitative structure-function analysis of H-Ras farnesyl-group for signal transduction in vivo. The approach makes use of enzymatic methods to attach structurally related farnesyl analogs onto the prenylation site of H-Ras combined with microinjection procedures to study their in vivo function. Oocytes are naturally arrested at the G2-M boundary of the first meiotic cell division. (See reference 80, infra). When microinjected with oncogenic H-Ras, oocytes reenter the cell cycle, which is monitored by germinal vesicle breakdown (GVBD) by the appearance of a white spot in the animal hemisphere. GVBD is accompanied by activation of the mitogen-activated protein kinase (MAPK) cascade. (See 81, 82, infra). Bacterially expressed H-Ras has been shown to activate these processes when microinjected into Xenopus oocytes. (See references 24, 45, infra). These biochemical effects are strictly dependent on in vivo farnesylation of the injected H-Ras protein since mutation of the CaaX prenylation motif, blocking isoprenoid biosynthesis, and inhibition of FTase in oocytes all suppress these activities. (See references 83–85, infra). Thus, the system provides a method to study the in vivo role of prenylation by analyzing the ability of FPP analogues to rescue H-Ras biological functions in isoprenoid-depleted oocytes.

Figure 9:
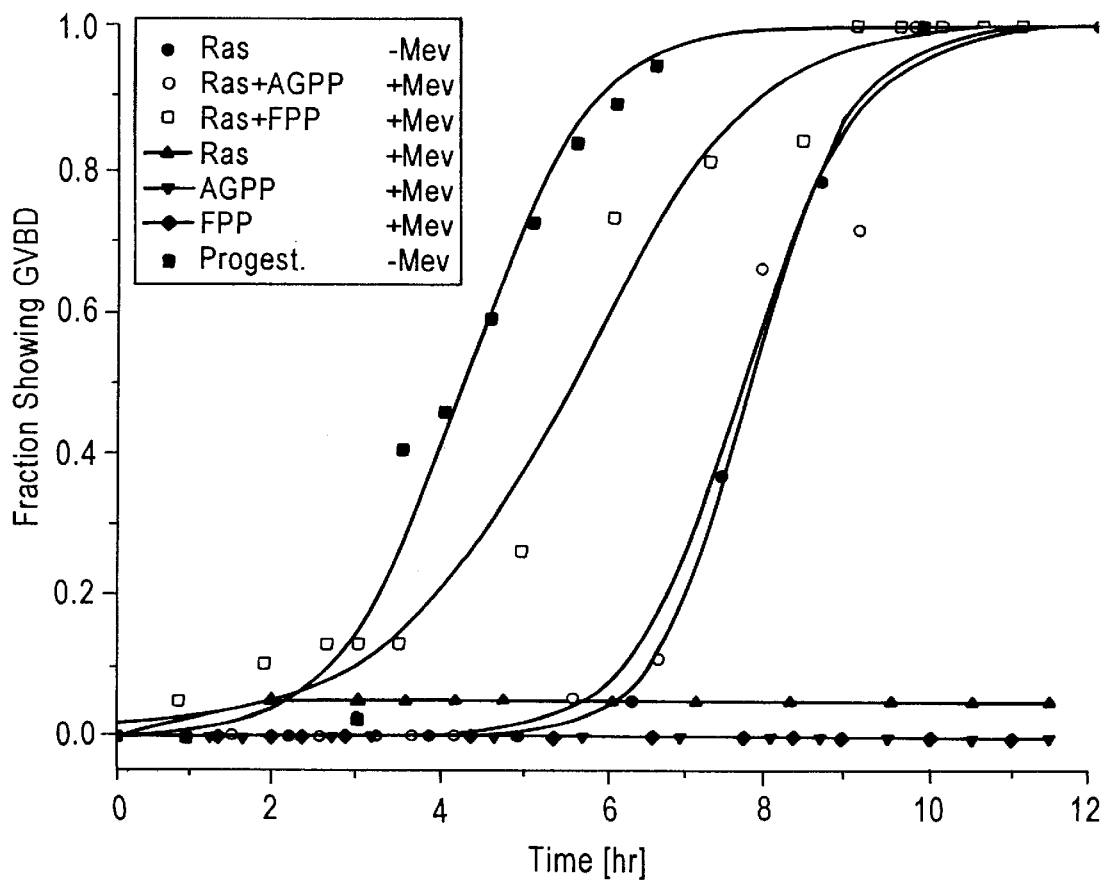
FIG. 9. AGPP Rescues the Biological Activity of Oncogenic H-Ras in Isoprenoid Depleted Oocytes with Delayed Maturation Kinetics Relative to FPP.

FIG. 9 shows that AGPP rescues the biological activity of oncogenic H-Ras in isoprenoid depleted oocytes with delayed maturation kinetics relative to FPP.

AGPP functions as well as FPP does when tested in the oocyte maturation assay, except for delayed maturation kinetics. These observations validate our hypothesis that prenylation with unnatural analogs leads to significant, biologically relevant effects. Oocytes were isolated from *X. laevis* females and allowed to recover overnight. (See 24, 45, infra). A sample (n=14) were treated with 10 $\mu$M progesterone to demonstrate the health of the oocytes and to ensure that they were capable of exhibiting GVBD (FIG. 9, filled squares). Overnight treatment with 50 $\mu$M mevinolin (an inhibitor of mevalonate biosynthesis) effectively depletes the endogenous pool of FPP; bacterially expressed oncogenic H-Ras (24 pmol) was unable to induce detectable maturation for at least 12 h after microinjection (FIG. 9, filled triangle), while the same H-Ras preparation typically induced 50% maturation after 6–8 h in untreated cells (FIG. 9, filled circle) However, co-microinjection of either FPP (FIG. 9, open square) or AGPP (FIG. 9, open circle) along with oncogenic H-Ras rescues the ability of H-Ras to induce oocyte maturation in mevinolin-treated cells, although with different kinetics of maturation. This effect was specific because neither FPP nor AGPP alone displayed any biological effect (FIG. 9). The maturation kinetics of oocytes stimulated with H-Ras and AGPP are slowed, with a time necessary to achieve 50% maturation that is 2–4 h longer than for oocytes injected with FPP. This result suggests that while AGPP is a fully functional FPP analog in vitro (see above), AGPP is not a complete farnesyl replacement when assayed for additional biological functions. It is not known if the reduced activity of AG-modified H-Ras reflects slow FTase kinetics in oocytes, a specific defect in Ras-effector interaction (such as activation of the Raf-MAPK cascade), or is the consequence of impaired downstream processing and membrane binding.

These data suggest that the structural requirements for FTase differ from those necessary for additional biological events and support the hypothesis that FPP analogs can be generated that may be inhibitors of the prenyl-protein specific enzymes downstream of protein farnesylation.

FIG. 7 depicts inhibition of Squalene Synthase by AGPP. The initial rates of squalene synthase activity were determined from bovine brain microsomal preparations in the presence of the indicated concentration of unlabeled AGPP (filled squares) or unlabeled FPP (open triangles) (77). Crude bovine brain microsomes and 0.05 mM [$^3$H]FPP (105 cpm/pmol) and unlabeled AGPP and FPP were added at the indicated concentrations and incubated for 30 min at 37 C. The reactions were terminated with 40% (wt/vol) KOH and 95% ethanol. Authentic carrier squalene (20 $\mu$g) was added and the reactions extracted with petroleum ether. The amount of labeled lipid formed was measured by scintillation counting.

AGPP does not Inhibit Squalene Synthase Activity. Inhibitors of Ras FTase (FTIs) have been designed based on the farnesyl moiety of the farnesyl pyrophosphate substrate. This class of inhibitors has attracted less interest due to the possible nonselective effects on additional farnesyl pyrophosphate utilizing enzymes particularly those involved in cholesterol biosynthesis such as squalene synthase (17). The pyrophosphate group is typically replaced in these FTIs by nonhydrolyzable moieties such as phosphinic acids or phosphonates. A number of these molecules have been shown to inhibit H-Ras mediated transformation of NIH 3T3 cells (111) without toxicity.

An important goal of this work is to generate molecules with exceptional selectivity for FTase over other FPP metabolizing pathways. Some previously characterized FTase inhibitors have been described as inhibitors of squalene synthase, an enzyme that utilizes FPP, and is an important secondary regulatory protein in the cholesterol biosynthetic pathway. (See 112, 113, infra). AGPP was found to be a far less potent in vitro inhibitor of squalene synthase activity than for FTase. (See, FIG. 7). (See also reference 77, infra). In addition, in vitro studies failed to detect any conversion of [$^3$H]AGPP to organic products. These results suggest that the prenyl binding site of squalene synthase is sufficiently different from that of FTase to allow very effective discrimination against AGPP.

SUMMARY

In this study, we describe the design, synthesis, and FTase dependent in-vitro transfer of the novel farnesyl pyrophosphate analog AGPP to H-Ras. We have developed an efficient five step synthesis of 8-aniline-geranyl pyrophosphate (AGPP) in good yield where the amino-nitrogen of AGPP is uncharged at physiological pH, due to its conjugation with the phenyl ring. The mildness and high chemoselectivity of the reductive amination reaction coupling the aniline to the geranyl skeleton will allow us to synthesize many additional functionalized isoprenyl analogs.

Synthetic modification of enzymatic substrates is useful in studying the interactions between small molecules and proteins because it allows critical structures involved in ligand binding and catalysis to be identified. The ability of FTase to transfer lipid analogs to target proteins is sensitive to the structure of the ω-terminal group of the prenyl chain. Moieties that are too large, too small, or with other incompatible functionality may be good inhibitors of transfer to protein substrate, but are themselves poorly transferred (39–47). Chemically conservative FPP analogs stripped of most isoprenoid features (methyl groups, unsaturation) to more resemble simple fatty acids are still transferred by FTase to Ras (16). However, these FPP analogs do not contain functionality that can be derivatized with groups useful for probing the chemistry of the binding pocket of FTase nor of the subsequent intermolecular interactions of the post-translationally modified target molecules.

The design of AGPP as an analog of FPP originated from our observation that esters and ethers formed from ω-hydroxylated geraniol and farnesol (39–47) share significant structural overlap with FPP and GGPP and act as inhibitors of FTase that are inefficiently transferred to protein substrates. The failure of the previously described FPP analogs to be efficiently transferred to H-Ras by FTase, in which ester linked functional groups replaced the terminal isoprene unit, prompted us to investigate the feasibility of synthesizing transferable molecules containing aromatic amino linkages. We focused our efforts on the aniline ring system, for which a large body of derivitization chemistry is known and which introduces a heteroatom linkage connecting the geranyl pyrophosphate moiety to the phenyl group replacing the terminal isoprene.

AGPP was found to be a highly selective FPP analog and a potent competitive inhibitor (alternate substrate) of FTase ($IC_{50}$=0.6 μM). AGPP is a significantly inferior substrate for the GGTase I ($IC_{50}$=31 μM) and the FPP utilizing enzyme squalene synthase ($IC_{50}$=1000 μM). The substrate selectivity of GGTase I for AGPP is similar to the enzyme's behavior towards FPP. However, the structural differences between AGPP and FPP do not allow AGPP to interfere with squalene synthase activity. AGPP is the first example of a class of compounds that are alternate substrates for protein isoprenylation that are not inhibitors of squalene synthase. Other compounds have been found through design and screening of chemical libraries that have yielded potent inhibitors of FTase that are not inhibitors of squalene synthase (48). Selective inhibition of FTase versus GGTase I has been also been reported for both CAAX-based tetrapeptides and farnesylpyrophosphate analogs [for a review, see (49)]. While the selectivity of AGPP for FTase is inferior to that for many CAAX peptidomimetics, it is comparable to that for other farnesyl pyrophosphate analogue inhibitors (50).

Previously described FPP analogs that are not efficient substrates for transfer show substantial structural similarity to FPP. Based on the structure of FPP and analogs that are transferred (vide supra) we can summarize some of the structural requirements for an analog that is efficiently transferred. FPP analogs where conservative changes in the hydrocarbon portion of the lipid that 1.) increase the lipophilicity of the molecule, 2.) do not add additional steric bulk to the molecule, and 3.) preserve the allylic pyrophosphate functionality, are transferred by FTase to Ras. However, analogs of FPP that 1.) greatly increase the steric bulk at the ω-terminus, 2.) increase the rigidity of the ω-terminal moiety, and/or 3.) introduce an ester linkage between the ω-terminus of the geranyl pyrophosphate moiety and the ω-terminal analog group prevent transfer. Structural characteristics of AGPP include 1.) no ester functionality, 2.) a somewhat greater polarity than a simple hydrocarbon, 3.) a phenyl ring only slightly larger than the terminal isoprene of FPP, and 4.) an aniline with approximately the same conformational rigidity of the ω-terminal isoprene of FPP. In addition, substitution of iodine onto the para-position of the phenyl ring allows binding of the substrate in a productive conformation, as demonstrated by the efficient transfer of I-AGPP by FTase to H-Ras. Recently, the crystal structure of FTase has been solved by three groups (51–53). Because AGPP and FPP, but not the ester linked analogs are transferred appropriately to Ras, we are poised to begin an initial structure-function analysis to understand the substrate selectivity of FTase.

AGPP and some of the other analog structures have been modeled into the available x-ray crystal structures of FTase. Comparison of the structures of the analogs tested permit making an initial approach to a SAR for transfer by FTase. This analysis suggests that a molecular ruler for lipid pyrophosphate substrate discrimination is operating. The longest analogs are 5 and 6 due to the linear three atom p-azido moiety on the aniline ring and may not fit in the lipid binding cleft of FTase in a productive way, much like GGPP. AGPP is very close in size to FPP, and is transferred efficiently.

Synthesis of the FPP analog AGPP that serves as a transferable substrate for FTase has been demonstrated. The development of these and similar probes should make it possible to undertake detailed studies of the structural domains of the binding sites of many enzymes and other proteins that utilize isoprenoids as substrates. Additional analogs based on AGPP should provide valuable probes to examine 1.) the functional role of protein-linked isoprenoids in vivo, 2.) the role of isoprenylation in the interaction of H-Ras with membranes, 3.) the enzymes involved in the subsequent C-terminal processing needed for plasma membrane localization and biological activity, and 4.) the cellular effector proteins (54).

As is apparent from the foregoing discussion, additional analogs can be easily envisioned as being within the scope of the present invention. Such molecules would be expected to be similarly useful in the study and understanding of protein prenylation.

The results of the foregoing experiments clearly show that 1) unnatural FPP analogs that are transferred by FTase to Ras can be synthesized, 2) the biochemical properties of transfer can be characterized and 3) analogs can be generated which partially restore Ras biological function in a tractable in vivo model system. It is believed that these unnatural, synthetic molecules will provide lead compounds that will permit better understanding of the biochemical role of isoprenylation and subsequent post-translational modifications and their biological function, and may provide information on the role of prenylation, and lead to the development of new rational and effective treatment strategies (FTIs).

REFERENCES

1. Barbacid, M. (1987) *Annu. Rev. Beiochem.* 56, 779–927.
2. Zhang, F. L., and Casey, P. J. (1996) *Annu. Rev. Biochem.* 65, 241–269.
3. Reiss, Y., Goldstein, J. L., Seabra, M. C., Casey, P. J., and Brown, M. S. (1990) *Cell* 62, 81–88.
4. Glomset, J. A., and Farnsworth, C. C. (1994) *Annu. Rev. Cell Biol.* 10, 181–205.
5. Jackson, J. H., Cochrane, C. G., Bourne, J. R., Solski, P. A., Buss, J. E., and Der, C. J. (1990) *Proc. Natl. Acad. Sci. USA* 87, 3042–3046.
6. Kato, K., Cox, A. D., Hisaka, M. M., Graham, S. M., Buss, J. E., and Der, C. J. (1992) *Proc. Natl. Acad. Sci. USA* 89, 6403–6407.
7. Schafer, W. R., Kim, R., Sterne, R., Thorner, J., Kim, S. H., and Rine, J. (1989) *Science* 245, 379–385.

8. Moomaw, J. F., and Casey, P. J. (1992) *J. Biol. Chem.* 267, 17438–17443.
9. Yokoyama, K., and Gelb, M. H. (1993) *J. Biol. Chem.* 268, 4055–4060.
10. Andres, D. A., Seabra, M. C., Brown, M. S., Armstrong, S. A., Smeland, T. E., Cremers, F. P., and Goldstein, J. L. (1993) *Cell* 73, 1091–1099.
11. Hancock, J. F., Magee, A. I., Childs, J. E., and Marshall, C. J. (1989) *Cell* 57, 1167–1177.
12. Hancock, J. F., Cadwallader, K., Paterson, H., and Marshall, C. J. (1991) *EMBO J.* 10, 4033–4039.
13. Hancock, J. F., Cadwallader, K., and Marshall, C. J. (1991) *EMBO J.* 10, 641–646.
14. Leevers, S. J., Paterson, H. F., and Marshall, C. J. (1994) *Nature* 369, 411–414.
15. Stokoe, D., Macdonald, S. G., Cadwallader, K., Symons, M., and Hancock, J. F. (1994) *Science* 264, 1463–1467.
16. Dudler, T., and Gelb, M. H. (1997) *Biochemistry* 36, 12434–12441.
17. Marshall, C. J. (1993) *Science* 259, 1865–1866.
18. Casey, P. J. (1995) *Science* 268, 221–225.
19. Crick, D. C., Suders, J., Kluthe, C. M., Andres, D. A., and Waechter, C. J. (1995) *J. Neurochem.* 65, 1365–1373.
20. Kamiya, Y., Sakurai, A., Tamura, S., Takahashi, N., Tsuchiya, E., Abe, K., and Fukui, S. (1979) *Agric. Biol. Chem.* 43, 363–369.
21. Umbreit, M. A., and Sharpless, K. B. (1977) *J. Am. Chem. Soc.* 99, 5526–5527.
22. Abdel-Magid, A. F., Maryanoff, C. A., and Carson, K. G. (1990) *Tetrahedron Lett.* 31, 5595–5598.
23. Abdel-Magid, A. F., and Maryanoff, C. A. (1990) *Synlett*, 537–539.
24. Abdel-Magid, A. F., Harris, B. D., and Maryanoff, C. A. (1994) *Synlett*, 81–83.
25. Abdel-Magid, A. F., Carson, K. G., Harris, B. D., Maryanoff, C. A., and Shah, R. D. (1996) *J. Org. Chem.* 61, 3849–3862.
26. Sandri, J., and Viala, J. (1992) *Syn. Commun.* 22, 2945–2948.
27. Davisson, V. J., Woodside, A. B., and Poulter, C. D. (1985) *Methods Enzymol.* 110, 130–144.
28. Davisson, V. J., Woodside, A. B., Neal, T. R., Stremler, K. E., Muehlbacher, M., and Poulter, C. D. (1986) *J. Org. Chem.* 51, 4768–4779.
29. Brown, M. J., Milano, P. D., Lever, D. C., Epstein, W. W., and Poulter, C. D. (1991) *J. Am. Chem. Soc.* 113, 3176–3177.
30. Threadgill, M. D., and Gledhill, A. P. (1989) *J. Org. Chem.* 54, 2940–2949.
31. Andres, D. A., Goldstein, J. L., Ho, Y. K., and Brown, M. S. (1993) *J. Biol. Chem.* 268, 1383–1390.
32. Armstrong, S. A., Hannah, V. C., Goldstein, J. L., and Brown, M. S. (1995) *J. Biol. Chem.* 270, 7864–7868.
33. Honda, A., Salen, G., Nguyen, L. B., Tint, G. S., Batta, A. K., and Shefer, S. (1998) *J. Lipid Res.* 39, 44–50.
34. Dunphy, P. J., Kerr, J. D., Pennock, J. F., Whittle, K. J., and Feeney, J. (1967) *Biochim. Biophys. Acta* 136, 136–147.
35. Calzada, J. G., and Hooz, J. (1988) *Org. Synth. Coll. Vol.* 6, 634–637.
36. Young, W. G., Caserio, F. F., and Brandon, D. D. (1960) *J. Am. Chem. Soc.* 82, 6163–6168.
37. Corey, E. J., Kim, C. U., and Takeda, M. (1972) *Tetrahedron Lett.* 42, 4339–4342.
38. Watson, N. S., and Procopiou, P. A. (1996) *Prog. Med. Chem.* 33, 331–378.
39. Baba, T., and Allen, C. M. (1984) *Biochemistry* 23, 1312–1322.
40. Baba, T., Muth, J., and Allen, C. M. (1985) *J. Biol. Chem.* 260, 10467–10473.
41. Allen, C. M. (1985) *Methods Enzymol.* Vol. 110, 117–124.
42. Bukhtiyarov, Y. E., Omer, C. A., and Allen, C. M. (1995) *J. Biol. Chem.* 270, 19035–19040.
43. Das, N. P., and Allen, C. M. (1991) *Biochem. Biophys. Res. Commun.* 181, 729–735.
44. Gaon, I., Turek, T. C., Weller, V. A., Edelstein, R. L., Singh, S. K., and Distefano, M. D. (1996) *J. Org. Chem.* 61, 7738–7745.
45. Gaon, I., Turek, T. C., and Distefano, M. D. (1996) *Tetrahedron Lett.* 37, 8833–8836.
46. Turek, T. C., Gaon, I., and Distefano, M. D. (1996) *Tetrahedron Lett.* 37, 4845–4848.
47. Edelstein, R. L., and Distefano, M. D. (1997) *Biochem. Biophys. Res. Commun.* 235, 377–382.
48. Koyama, T., Ogura, K., and Seto, S. (1980) *Biochim. Biophys. Acta* 617, 218–224.
49. Ayral-Kaloustian, S., and Skotnicki, J. S. (1996) in *Annual Reports in Medicinal Chemistry* (Bristol, J. A., Ed.) Vol. 31, pp. 171–180, Academic Press, Inc., San Diego.
50. Sebti, S. M., and Hamilton, A. D. (1997) *Pharmacol. Ther.* 74, 103–114.
51. Park, H.-W., Boduluri, S. R., Moomaw, J. F., Casey, P. J., and Beese, L. S. (1997) *Science* 275, 1800–1804.
52. Long, S. B., Casey, P. J., and Beese, L. S. (1998) *Biochemistry* 37, 9612–9618.
53. Dunten, P., Kammlott, U., Crowther, R., Weber, D., Palermo, R., and Birktoft, J. (1998) *Biochemistry* 37, 7907–7912.
54. Wedegaertner, P. B., Wilson, P. T., and Bourne, H. R. (1995) *J. Biol. Chem.* 270, 503–506.
55. Chen W J, Andres D A, Goldstein J L, Russell D W, Brown M S. cDNA cloning and expression of the peptide-binding beta subunit of rat p21ras farnesyltransferase, the counterpart of yeast DPR1/RAM1. Cell Jul. 26, 1991;66 (2):327–34.
56. Leonard, D. M., Ras Farnesyltransferase: A New Therapeutic Target. J Med chem 40, 2971–2990 (1997)
57. Dudler, T.; Gelb, M. H. Palmitoylation of Ha-Ras facilitates membrane binding, activation of downstream effectors, and meiotic maturation in Xenopus oocytes. J. Biol. Chem. 1996, 271, 11541–11547.
58. Chen W J, Andres D A, Goldstein J L, Brown M S. Cloning and expression of a cDNA encoding the alpha subunit of rat p21ras protein farnesyltransferase. Proc Natl Acad Sci USA Dec. 15, 1991;88(24):11368–72.
59. Andres D A, Goldstein J L, Ho Y K, Brown M S. Mutational analysis of alpha-subunit of protein farnesyltransferase. Evidence for a catalytic role. J Biol Chem Jan. 15, 1993;268(2):1383–90.
60. Dudler, T., and Gelb, M. H. Replacement of the H-Ras farnesyl group by lipid analogues: implications for downstream processing and effector activation in Xenopus oocytes. (1997) *Biochemistry* 36, 12434–12441.
61. Baba, T., and Allen, C. M. (1984). Inactivation of Undecaprenylpyrophosphate Synthetase with a Photolabile Analogue of Farnesyl Pyrophosphate. *Biochemistry* 23(6), 1312–1322.
62. Baba, T., Muth, J., and Allen, C. M. (1985). Photoaffinity Labeling of Undecaprenyl Pyrophosphate Synthetase with a Farnesyl Pyrophosphate Analogue. *J. Biol. Chem.* 260(19), 10467–10473.
63. Allen, C. M. (1985). Photolabile Analogs of the Allylic Pyrophosphate Substrate of Prenyltransferases. *Methods Enzymol.* Vol. 110, 117–124.

64. Bukhtiyarov, Y. E., Omer, C. A., and Allen, C. M. (1995). Photoreactive Analogues of Prenyl Diphosphates as Inhibitors and Probes of Human Protein Farnesyltransferase and Geranylgeranyltransferase Type I. *J. Biol. Chem.* 270(32), 19035–19040.
65. Das, N. P., and Allen, C. M. (1991). Inhibition of Farnesyl Transferases from Malignant and Non-malignant Cultured Human Lymphocytes by Prenyl Substrate Analogues. *Biochem. Biophys. Res. Commun.* 181(2), 729–735.
66. Gaon, I., Turek, T. C., Weller, V. A., Edelstein, R. L., Singh, S. K., and Distefano, M. D. (1996). Photoactive Analogs of Farnesyl Pyrophosphate Containing Benzoylbenzoate Esters: Synthesis and Application to Photoaffinity Labeling of Yeast Protein Farnesyltransferase. *J. Org. Chem* 61(22), 7738–7745.
67. Gaon, I., Turek, T. C., and Distefano, M. D. (1996). Farnesyl and Geranylgeranyl Pyrophosphate Analogs Incorporating Benzoylbenzyl Ethers: Synthesis and Inhibition of Yeast Protein Farnesyltransferase. *Tetrahedron Lett.* 37(49), 8833–8836.
68. Turek, T. C., Gaon, I., and Distefano, M. D. (1996). Analogs of Farnesyl Pyrophosphate Incorporating Internal Benzoylbenzoate Esters: Synthesis, Inhibition Kinetics and Photoinactivation of Yeast Protein Farnesyltransferase. *Tetrahedron Lett.* 37(28), 4845–4848.
69. Edelstein, R. L., and Distefano, M. D. (1997). Photoaffinity Labeling of Yeast Farnesyl Protein Transferase and Enzymatic Synthesis of a Ras Protein Incorporating a Photoactive Isoprenoid. *Biochem. Biophys. Res. Commun.* 235(2), 377–382.
70. Calzada, J. G., and Hooz, J. (1988). Geranyl Chloride. *Org. Synth.* Coll. Vol. 6, 634–637.
71. Young, W. G., Caserio, F. F., and Brandon, D. D. (1960). Allylic Rearrangements. XLIX. The Controlled Conversion of α- and γ-Methylallyl Alcohols to Chlorides with Thionyl Chloride. *J. Am. Chem. Soc.* 82(4), 6163–6168.
72. Corey, E. J., Kim, C. U., and Takeda, M. (1972). A Method for Selective Conversion of Allylic and Benzylic Alcohols to Halides Under Neutral Conditions. *Tetrahedron Lett.* 42, 4339–4342.
73. Sandri, J., and Viala, J. (1992). Convenient Conversion of Cis-Homoallylic Alcohols into Corresponding Bromides with $Ph_3PBr_2$. *Syn. Comun.* 22(20), 2945–2948.
74. Andres D A, Crick D C, Finlin B S, Waechter C J. Rapid identification of cysteine-linked isoprenyl groups by metabolic labeling with [$^3$H]farnesol and [$^3$H]geranylgeraniol. Methods Mol Biol 1999;116:107–23.
75. Crick D C, Suders J, Kluthe C M, Andres D A, Waechter C J. Selective inhibition of cholesterol biosynthesis in brain cells by squalestatin 1. J Neurochem September 1995;65(3): 1365–73.
76. Cassidy P B, Dolence J M, Poulter C D. Continuous fluorescence assay for protein prenyltransferases. Methods Enzymol 1995;250:30–43.
77. Pompliano, D L, Gomez, R P, Anthony, N J. Intramolecular Fluorescence Enhancement: A Continuous Assay of Ras Farnesyl:Protein Transferase. J. Am. Chem. Soc. 1992, 114, 7945–7946.
78. Birchmeier C, Broek D, Wigler M. ras proteins can induce meiosis in Xenopus oocytes. Cell. December 1985;43(3 Pt 2):615–21.
79. McGeady P, Kuroda S, Shimizu K, Takai Y, Gelb M H. The farnesyl group of H-Ras facilitates the activation of a soluble upstream activator of mitogen-activated protein kinase. J Biol Chem Nov. 3, 1995;270(44):26347–51.
80. McGeady P, Porfiri E, Gelb M H. The farnesyl group activates Ras towards guanine nucleotide exchange catalyzed by the sos protein. Bioorg Med Chem Lett. 1997, &, 145–150.
81. Gibbs J B, Schaber M D, Schofield T L, Scolnick E M, Sigal I S. Xenopus oocyte germinal-vesicle breakdown induced by [Val12]Ras is inhibited by a cytosol-localized Ras mutant. Proc Natl Acad Sci USA. September 1989;86 (17):6630–4.
82. Zhao J, Kung H F, Manne V. Farnesylation of p21 Ras proteins in Xenopus oocytes. Cell Mol Biol Res. 1994;40 (4):313–21.
83. Kim R, Rine J, Kim S H. Prenylation of mammalian Ras protein in Xenopus oocytes. Mol Cell Biol. November 1990;10(11):5945–9.
84. Manne, V.; Ricca, C. S.; Brown, J. G.; Tuomari, A. V.; Yan, N.; Patel, D.; Schmidt, R.; Lynch, M. J.; Ciosek, C. P., Jr.; Carboni, J. M.; Robinson, S.; Gordon, E. M.; Barbacid, M.; Seizinger, B. R.; Biller, S. A. Ras farnesylation as a target for novel antitumor agents: Potent and selective farnesyl diphosphate analog inhibitors of farnesyltransferase. Drug Dev. Res. 1995, 34, 121–137.
85. Watson, N. S., and Procopiou, P. A. Squalene synthase inhibitors: their potential as hypocholesterolaemic agents. (1996) *Prog. Med. Chem.* 33, 331–378.
86. Koyama, T., Ogura, K., and Seto, S. (1980). Substrate Specificity of Squalene Synthetase. *Biochim. Biophys. Acta* 617(2), 218–224.
87. Andres D A, Shao H, Crick D C, Finlin B S. Expression cloning of a novel farnesylated protein, RDJ2, encoding a DnaJ protein homologue. Arch Biochem Biophys Oct. 1, 1997;346(1):113–24.
88. Leonard, D. M., Ras Farnesyltransferase: A New Therapeutic Target. J Med chem 40, 2971–2990 (1997).
89. Buss J E, Marsters J C Jr. Farnesyl transferase inhibitors: the successes and surprises of a new class of potential cancer chemotherapeutics. Chem Biol Dec. 2, 1995;(12): 787–91.
90. Gibbs, J B, Graham, S L, Hartman, G D, Koblan, K S, Kohl, N E, Omer, C A and Oliff, A. Farnesyltransferase inhibitors versus Ras inhibitors. Current opinion in Chemical Biology 1997, 1, 197–203.
91. Gibbs J B, Oliff A. The potential of farnesyltransferase inhibitors as cancer chemotherapeutics. Annu Rev Pharmacol Toxicol 1997;37:143–66.
92. Kohl, N. E.; Mosser, S. D.; deSolms, S. J.; Giuliani, E. A.; Pompliano, D. L.; Graham, S. L.; Smith, R. L.; Scolnick, E. M.; Oliff, A.; Gibbs, J. B. Selective inhibition of Ras-dependent transformation by a farnesyltransferase inhibitor. Science 1993, 260, 1934–1937.
93. Graham, S. L.; deSolms, S. J.; Giuliani, E. A.; Kohl, N. E.; Mosser, S. D.; Oliff, A. I.; Pompliano, D. L.; Rands, E.; Breslin, M. J.; Deana, A. A.; Garsky, V. M.; Scholz, T. H.; Gibbs, J. B.; Smith, R. L. Pseudopeptide inhibitors of Ras farnesyl-protein transferase. J. Med. Chem. 1994, 37, 725–732.
94. Prendergast, G. C.; Davide, J. P.; deSolms, S. J.; Giuliani, E. A.; Graham, S. L.; Gibbs, J. B.; Oliff, A.; Kohl, N. E. Farnesyl-transferase inhibition causes morphological reversion of Ras-transformed cells by a complex mechanism that involves regulation of the actin cytoskeleton. Mol. Cell Biol. 1994, 14, 4193–4202.
95. Kohl, N. E.; Wilson, F. R.; Mosser, S. D.; Giuliani, E.; deSolms, S. J.; Conner, M. W.; Anthony, N. J.; Holtz, W. J.; Gomez, R. P.; Lee, T.-J.; Smith, R. L.; Graham, S. L.; Hartman, G. D.; Gibbs, J. B.; Oliff, A. Protein farnesyltransferase inhibitors block the growth of Ras-dependent tumors in nude mice. Proc. Natl. Acad. Sci. U.S.A. 1994, 91, 9141–9145.
96. Sun, J.; Qian, Y.; Hamilton, A. D.; Sebti, S. M. Ras CAAX peptidomimetic FTI-276 selectively blocks tumor growth in nude mice of a human lung carcinoma with K-Ras mutation and p53 deletion. Cancer Res. 1995, 55, 4243–4247.
97. Kohl, N. E.; Omer, C. A.; Conner, M. W.; Anthony, N. J.; Davide, J. P.; deSolms, S. J.; Giuliani, E. A.; Gomez, R. P.; Graham, S. L.; Hamilton, K.; Handt, L. K.; Hartman, G. D.; Koblan, K. S.; Kral, A. M.; Miller, P. J.; Mosser, S. D.; O'Neill, T. J.; Rands, E.; Schaber, M. D.; Gibbs, J. B.; Oliff, A. Inhibition of farnesyl-transferase induces regression of mammary and salivary carcinomas in Ras transgenic mice. Nature Medicine 1995, 1, 792–797.
98. Sepp-Lorenzino, L.; Ma, Z.; Rands, E.; Kohl, N. E.; Gibbs, J. B.; Oliff, A.; Rosen, N. A peptidomimetic inhibitor of farnesyl:protein transferase blocks the anchorage-dependent and -independent growth of human tumor cell lines. Cancer Res. 1995, 55, 5302–5309.
99. Clark G J, Kinch M S, Rogers-Graham K, Sebti S M, Hamilton A D, Der C J. The Ras-related protein Rheb is farnesylated and antagonizes Ras signaling and transformation. J Biol Chem. Apr. 18, 1997;272(16):10608–15.
100. Lebowitz P F, Casey P J, Prendergast G C, Thissen J A. Farnesyltransferase inhibitors alter the prenylation and growth-stimulating function of RhoB. J Biol Chem. Jun. 20, 1997; 272(25):15591–4.
101. Tan E W, Perez-Sala D, Canada F J, Rando R R. Identifying the recognition unit for G protein methylation. J Biol Chem Jun. 15, 1991;266(17):10719–22.
102. Perez-Sala D, Tan E W, Canada F J, Rando R R. Methylation and demethylation reactions of guanine nucleotide-binding proteins of retinal rod outer segments. Proc Natl Acad Sci USA Apr. 15, 1991;88(8):3043–6.
103. Volker, C.; Lane, P.; Kwee, C.; Johnson, M.; Stock, J. A single activity carboxyl methylates both farnesyl and geranylgeranyl cysteine residues. FEBS Lett. 1991, 295, 189–194.
104. Perez-Sala, D.; Gilbert, B. A.; Tan, E. W.; Rando, R. R. Prenylated protein methyltransferases do not distinguish between farnesylated and geranylgeranylated substrates. Biochem. J. 1992, 284, 835–840.
105. Ma Y T, Gilbert B A, Rando R R. Farnesylcysteine analogs to probe role of prenylated protein methyltransferases. Methods Enzymol 1995;250:226–34.
106. Stephenson R C, Clarke S. Characterization of a rat liver protein carboxyl methyltransferase involved in the maturation of proteins with the -CXXX C-terminal sequence motif. J Biol Chem Jul. 5, 1992;267(19): 13314–9.
107. (a) Gibbs, R. A.; Krishnan, U.; Dolence, J. M.; Poulter, C. D. J. Org. Chem. 1995, 60, 7821. (b) Mu, Y. Q.; Gibbs, R. A.; Eubanks, L. M.; Poulter, C. D. J. Org. Chem. 1996, 61, 8010. (c) Shao, Y.; Eummer, J. T.; Gibbs, R. A. Org. Lett. 1999, 1, 627.
108. (a) Meinwald, J.; Opheim, K.; Eisner, T. Tetrahedron Lett. 1973, 4, 281. (b) Meinwald, J.; Thompson, W. R.; Eisner, T.; Owen, D. F. Tetrahedron Lett. 1971, 3485. (c) Bhalerao, U. T.; Rapoport, H. J. Am. Chem. Soc. 1971, 93, 4835.
109. Umbreit, M. A.; Sharpless, K. B. J Am. Chem. Soc. 1977, 99, 5526.
110. (a) Abdel-Magid, A. F.; Maryanoff, C. A.; Carson, K. G. Tetrahedron Lett. 1990, 31, 5595. (b) Abdel-Magid, A. F.; Maryanoff, C. A. Synlett 1990, 537. (c) Abdel-Magid, A. F.; Harris, B. D.; Maryanoff, C. A. Synlett 1994, 81. (d) Abdel-Magid, A. F.; Carson, K. G.; Harris, B. D.; Maryanoff, C. A.; Shah, R. D. J. Org. Chem. 1996, 61, 3849.
111. Ranu, B. C.; Majee, A.; Sarkar, A. J. Org. Chem 1998, 63, 370.
112. Calzada, J. G.; Hooz, J. Org. Synth. 1988, Coll. Vol. 6, 634.
113. Young, W. G.; Caserio, F. F.; Brandon, D. D. J. Am. Chem. Soc. 1960, 82, 6163.
114. Corey, E. J.; Kim, C. U.; Takeda, M. Tetrahedron Lett. 1972, 42, 4339.
115. Sandri, J.; Viala, J. Syn. Commun. 1992, 22, 2945.
116. (a) Davisson, V. J.; Woodside, A. B.; Poulter, C. D. Methods Enzymol. 1985, 110, 130. (b) Davisson, V. J.; Woodside, A. B.; Neal, T. R.; Stremler, K. E.; Muehlbacher, M.; Poulter, C. D. J. Org. Chem. 1986, 51, 4768.
117. Dolence J M, Poulter C D. A mechanism for posttranslational modifications of proteins by yeast protein farnesyltransferase. Proc. Natl. Acad. Sci. U.S.A. 1995, 92, 5008–5011.

What is claimed is:

1. A compound of the formula:

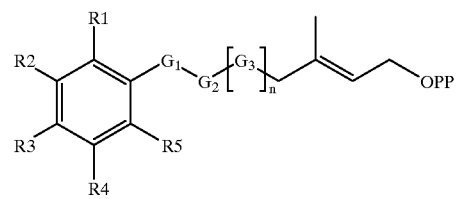

wherein R1–R5 are independently H, halo, $NO_2$, $NH_2$, $NHR_7$, $N(R_7)_2$, $N(R_7)_3^+$, $N_3$, OH, $OR_7$, $C_1$ to $C_8$ alkyl, amino $C_1$–$C_8$ alkyl, hydroxy $C_1$–$C_8$ alkyl, nitrile $C_1$–$C_8$ alkyl;

$G_1$ is $NR^6$ or —$CH_2$—O—;

$G_2$ is: —$CH_2$—, —$CH_2CH_2$— or

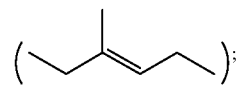

$G_3$ is: —O—$CH_2$—$CH_2$— or —$CH_2$—;

n is an integer of 0 to 14, inclusive;

$R_6$ is H or $C_1$ to $C_8$ alkyl;

$R_7$ is $C_1$–$C_8$ alkyl or $C_1$–$C_8$ alkanoyl;

OPP is the pyrophosphate group;

or a pharmaceutically acceptable salt thereof.

2. A compound according to claim 1, having the formula:

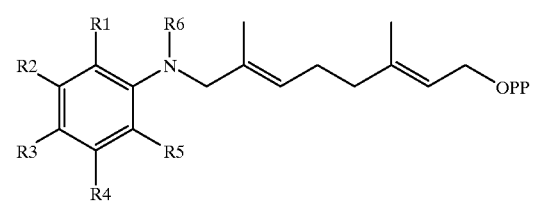

or a pharmaceutically acceptable salt thereof.

3. A compound according to claim 2 having the formula:

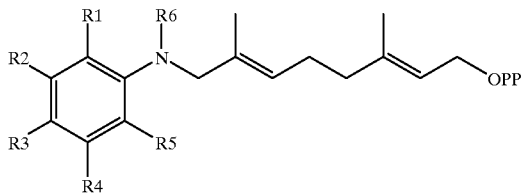

wherein $R_1$–$R_5$ are independently H, $C_1$ to $C_8$ alkyl, F, Cl, Br, I, $NO_2$, $N_3$ or $NH_3$;

$R_6$ is H, methyl or ethyl; and or a pharmaceutically acceptable salt thereof.

4. A compound according to claim 3, having the formula:

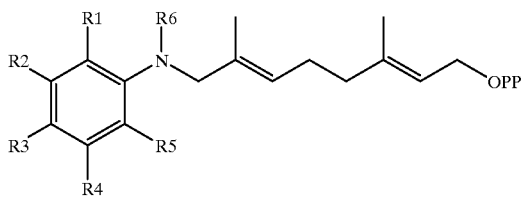

wherein $R_1$, $R_2$, $R_4$, and $R_5$ are H or F;

$R_3$ is H, $NO_2$, I, F or $N_3$; and $R_6$ is H, methyl or ethyl;

or a pharmaceutically acceptable salt thereof.

5. A compound which is:

8-aniline-3,7-dimethyl-2,6-octadiene pyrophosphate (AGPP);
8-(4-nitroaniline)-3,7-dimethyl-2,6-octadiene pyrophosphate;
8-(4-iodoaniline)-3,7-dimethyl-2,6-octadiene pyrophosphate;
8-pentafluoroaniline-3,7-dimethyl-2,6-octadiene pyrophosphate;
8-(4-azido-2,3,5,6-tetrafluoroaniline)-3,7-dimethyl-2,6-octadiene pyrophosphate; or
8-(N-ethyl-4-azido-2,3,5,6-tetrafluoroaniline)-3,7-dimethyl-2,6-octadiene pyrophosphate;

or a pharmaceutically acceptable salt thereof.

6. A compound according to claim 1, having the formula:

wherein n is an integer of 1 to 10;

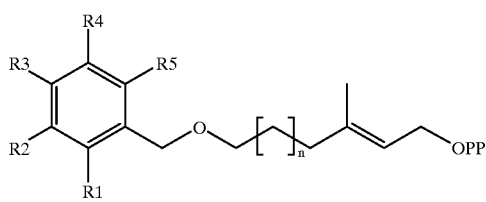

or a pharmaceutically acceptable salt thereof.

7. A compound according to claim 6, having the formula:

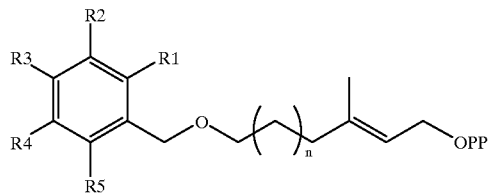

wherein n is an integer of 1 to 5;

or a pharmaceutically acceptable salt thereof.

8. A compound according to claim 7 having the formula:

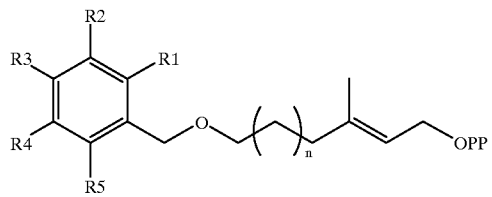

wherein $R^3$ is $C_1$ to $C_8$ alkyl, halo, $NO_2$, $N_3$ or $NH_3$;

$R^1$, $R^2$, $R^4$, and $R^5$ are H, $C_1$ to $C_8$ alkyl, halo, $NO_2$, $N_3$ or $NH_3$;

n is an integer of 1 to 5;

or a pharmaceutically acceptable salt thereof.

9. A compound which is:

6-benzyloxy-3-methyl-2-hexene pyrophosphate;
7-benzyloxy-3-methyl-2-heptene pyrophosphate;
8-benzyloxy-3-methyl-2-octene pyrophosphate;
9-benzyloxy-3-methyl-2-nonene pyrophosphate; or
10-benzyloxy-3-methyl-2-decene pyrophosphate, or a pharmaceutically acceptable salt thereof.

10. A compound according to claim 1 having formula:

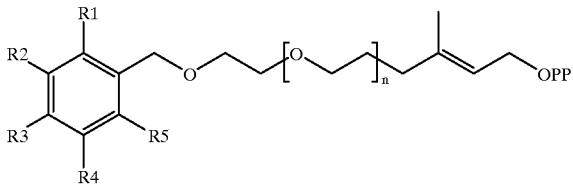

wherein n is an integer from 1 to 5;

or a pharmaceutically acceptable salt thereof.

11. A compound according to claim 1, having the formula:

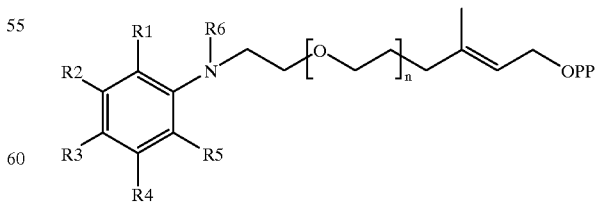

wherein $R_6$ is H or $C_1$ to $C_8$ alkyl;

and n is an integer from 1 to 5;

or a pharmaceutically acceptable salt thereof.

12. A compound according to claim 1, having the formula:

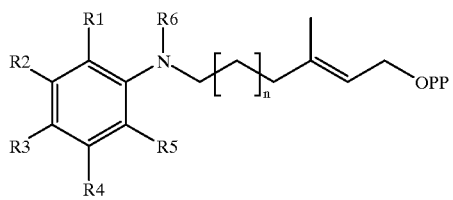

wherein $R_6$ is H or $C_1$ to $C_8$ alkyl; and
n is an integer number 1 to 10;
or a pharmaceutically acceptable salt thereof.

13. A compound of the formula:

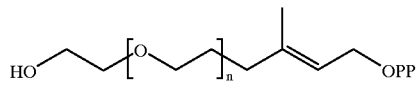

wherein n is an integer of 1 to 5.

14. A compound of the formula:

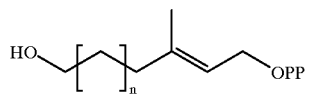

wherein n is an integer of 1 to 10.

15. A process of making a product having the formula:

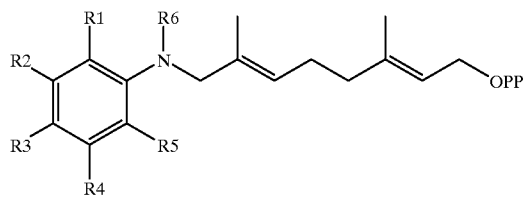

which comprises:
(a) oxidizing geranyl acetate to form (E,E)-3,7-Dimethyl-1-acetoxyl-2,6-octadiene-8-al;
(b) subjecting (E,E)-3,7-Dimethyl-1-acetoxyl-2,6-octadien-8-al to reductive amination by a substituted or unsubstituted aniline of the formula:

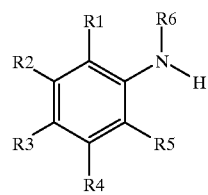

(c) replacing the acetoxy group with an hydroxy group;
(d) replacing the hydroxy group with a chloro;
(e) replacing the chloro with a pyrophosphate group to produce a said product;

wherein $R_1$–$R_5$ are H, $C_1$ to $C_8$ alkyl, halo, $NO_2$, $N_3$ or $NH_3$;
$R_6$ is H, $C_1$–$C_8$ alkyl.

16. A process of making a product having the formula:

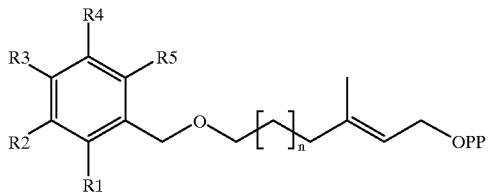

wherein R1–R5 and n are as defined in claim 1, which comprises:
(a) reacting a compound of the formula:

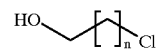

with a substituted or unsubstituted benzyl alcohol to form an intermediate:

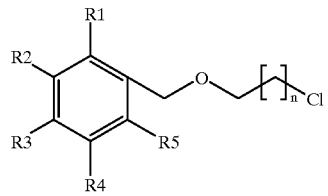

(b) reacting the intermediate from step (a) with ethyl aceto acetate to form an intermediate:

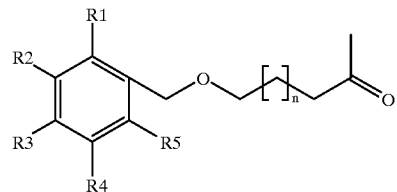

(c) extending the chain of the intermediate of step (b) with diisopropylphosphonoacetate and pyrophosphorylation to form said product.

17. A pharmaceutical composition comprising a compound according to claim 1, 2, 3, or 6, or a pharmaceutically acceptable salt thereof in admixture with one or more pharmaceutically acceptable solvent, carrier or diluent in a pharmaceutically effective amount.

* * * * *